(12) United States Patent
Binggeli et al.

(10) Patent No.: US 6,890,947 B2
(45) Date of Patent: May 10, 2005

(54) INDOLYL DERIVATIVES

(75) Inventors: Alfred Binggeli, Binningen (CH); Beat Wirz, Reinach (CH); Uwe Grether, Loerrach (DE); Hans Hilpert, Muenchenstein (CH); Roland Humm, Freiburg (DE); Hans Iding, Rheinfelden (DE); Bernd Kuhn, Riehen (CH); Hans-Peter Maerki, Basle (CH); Markus Meyer, Neuenburg (DE); Peter Mohr, Basle (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 6 days.

(21) Appl. No.: 10/659,664

(22) Filed: Sep. 10, 2003

(65) Prior Publication Data

US 2004/0053979 A1 Mar. 18, 2004

(30) Foreign Application Priority Data

Sep. 12, 2002 (EP) .............................................. 02020477

(51) Int. Cl.$^7$ ..................... A61K 31/404; C07D 209/04
(52) U.S. Cl. ....................................... 514/414; 548/465
(58) Field of Search ........................... 514/414; 548/465

(56) References Cited

U.S. PATENT DOCUMENTS

| | | | |
|---|---|---|---|
| 4,011,326 A | 3/1977 | Jensen | |
| 4,598,089 A | 7/1986 | Hadvary et al. | |
| 5,089,514 A | 2/1992 | Hulin | |
| 5,599,826 A | 2/1997 | Mertens et al. | |
| 5,811,439 A | 9/1998 | Ogawa et al. | |
| 5,856,529 A | 1/1999 | Catt et al. | |
| 6,004,996 A | 12/1999 | Shah et al. | |
| 6,069,156 A | 5/2000 | Oku et al. | |
| 6,121,397 A | 9/2000 | MacLeod et al. | |
| 6,291,685 B1 | 9/2001 | Junghans et al. | |
| 6,441,185 B1 | 8/2002 | Kühnle et al. | |

FOREIGN PATENT DOCUMENTS

| | | |
|---|---|---|
| EP | 185359 | 6/1986 |
| EP | 189577 | 8/1986 |
| EP | 443449 | 8/1991 |
| EP | 524495 | 1/1993 |
| EP | 0903343 | 3/1999 |
| EP | 1 078 923 | 2/2001 |
| WO | WO 91/19702 | 12/1991 |
| WO | WO 94/01420 | 1/1994 |
| WO | WO 94/13650 | 6/1994 |
| WO | WO 95/17394 | 6/1995 |
| WO | WO 96 26207 | 8/1996 |
| WO | WO 97/25042 | 7/1997 |
| WO | WO 97 27857 | 8/1997 |
| WO | WO 99/08501 | 2/1999 |
| WO | WO 99/10339 | 3/1999 |
| WO | WO 00 08002 | 2/2000 |
| WO | WO 00/09122 | 2/2000 |
| WO | WO 00/09123 | 2/2000 |
| WO | WO 0100603 | 1/2001 |
| WO | WO 02 08188 | 1/2002 |
| WO | WO 02 16331 | 2/2002 |
| WO | WO 03/004458 | 1/2003 |
| WO | WO 03 040114 | 5/2003 |
| WO | WO 03/053976 | 7/2003 |

OTHER PUBLICATIONS

Keller and Wahli: Trends Endocrin. Metab. (1993); 4:291–296.
MacDougald and Lane: Current Biology vol. 5 pp. 618–621 (1995).
Guerre–Millo, et. al.; J Biol Chem2000; 275: 16638–16642.
Balfour, et. al.; Drugs 57 (1999) 921–930.
Haigh et. al., Tetrahedron: Asymmetry, 10, pp. 1353–1367, 1999.
Gotteland et al., Synlett, 9 pp. 931–932 (1995).
Hulin et al., J. Med. Chem., 39, pp. 3897–3907 (1996).
Nicolaou et al., J. Am. Chem. Soc., 122, pp. 3830–3838 (2000).
Nichols et al., Anal. Biochem., 257, pp. 112–119 (1998).
Einsiedel et. al., Bioorg. Med. Chem. Lett., 10, pp. 2041–2044 (2000).
Goto et al., Chem. Pharm. Bull., 19, pp. 2050–2057 (1971).
Reichstein et al., Helvetica Chimica Acta, 16, pp. 121–129 (1933).
Diels et al., chem.. Ber., 48, pp. 897–905 (1915).
Wightman et al., J. Org. chem.., 43, pp. 2167–2170 (1978).
Musser et al., J. Med. Chem. 30, pp. 62–67 (1987).
Rahman et al., J. Chem. Soc. Perkin Trans. 1, 12, pp. 2973–1977 (1983).
Kelly et. al., J. Am. Chem. Soc., 110, pp. 6471–6480 (1988).
Kneen et al., Synthetic Communications, 16, pp. 1635–1640 (1986).

(Continued)

Primary Examiner—Taofiq Solola
(74) Attorney, Agent, or Firm—George W. Johnston; Dennis P. Tramaloni; Samuel H. Megerditchian

(57) ABSTRACT

Compounds of formula I are provided

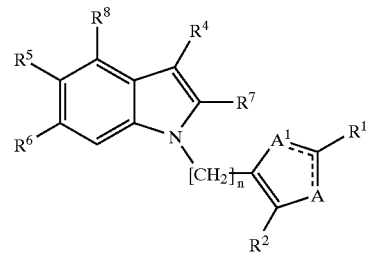

(I)

as well as pharmaceutically acceptable salts and esters thereof, wherein $R^1$ to $R^8$, A, $A^1$ and n have the significance indicated in the specification.

42 Claims, No Drawings

OTHER PUBLICATIONS

Kim et al., Can. J. Chem., 60, pp. 2093–2098 (1982).
Pàrkànyi et al., Monatsh. Chem., 123, pp. 637–645 (1992).
STN International ® CAPLUS Database, Accession No. 2000; 117035; Collins et al., WO 2000008002, abstract.
Malamas, MS et al, Eur. J. Med. Chem. vol. 36, No. 1 (2001) pp. 31–42.
Hulin, B. et al., Current Pharmaceutical Design, vol. 2 (1996) pp. 85–102.

Oplinger, et. al., ACS National Meeting, San Diego, Apr. 1–5, 2001, Poster 238, Division of Medicinal Chemistry, Section C.

Gustavsson, et. al., Chemical Abstracts, vol. 138, No. 106, 504 (2003).

Oku, Teruo et, Database CA, Abstract XP002265626.

Henke B R et al, Bioorganic & Medicinal Chemistry Letters, vol. 9 (23) (Dec. 1999).

INDOLYL DERIVATIVES

BACKGROUND OF INVENTION

Peroxisome Proliferator Activated Receptors (PPAR's) are members of the nuclear hormone receptor super family, which are ligand-activated transcription factors regulating gene expression. Various subtypes thereof have been identified and cloned. These include PPARα, PPARβ (also known as PPARδ), and PPARγ. There exist at least two major isoforms of PPARγ. While PPARγ1 is ubiquitously expressed in most tissues, the longer isoform PPARγ2 is almost exclusively found in adipocytes. In contrast, PPARα is predominantly expressed in the liver, kidney and heart. PPAR's modulate a variety of body responses including glucose- and lipid-homeostasis, cell differentiation, inflammatory responses and cardiovascular events.

Diabetes is a disease in which a patient's ability to control glucose levels in blood is impaired, because he has partially lost the ability to respond properly to the action of insulin. In type II diabetes (T2D), often referred to as non-insulin dependent diabetes mellitus (NIDDM), which afflicts 80–90% of all diabetic patients in developed countries, the Isles of Langerhans in the pancreas still produce insulin. However, the target organs, mainly muscle, liver and adipose tissue, exhibit a profound resistance to insulin stimulation, and the body compensates by producing unphysiologically high levels of insulin. In later stage of disease, however, insulin secretion decreases due to exhaustion of the pancreas. In addition to that T2D is a metabolic-cardiovascular disease sysndrome. Among the comorbidities associated with T2D are for example insulin resistance, dyslipidemia, hypertension, endothelial dysfunction and inflammatory atherosclerosis.

Current first line treatment for diabetes generally involves low fat- and glucose-diet and exercise. However, compliance can be moderate and as the disease progresses, treatment with hypoglycemic drugs, e.g. sulfonylureas or metformin, becomes necessary. A promising new class of drugs has recently been introduced that resensitizes patients to their own insulin (insulin sensitizers), thereby reverting blood glucose and triglyceride levels to normal, and thus abolishing, or at least reducing, the requirement for exogenous insulin. Pioglitazone (Actos™) and rosiglitazone (Avandia™) belong to the thiazolidinediones (TZD) class of PPARγ-agonists and were the first representatives who had been approved for NIDDM in several countries. These compounds, however, suffer from side effects including rare but severe liver toxicity (as seen with troglitazone), and they increase body weight in humans. Therefore, new, better and more efficacious drugs for the treatment of NIDDM are urgently needed. Recent studies provide evidence that a coagonism on PPARα and PPARγ would result in compounds with enhanced therapeutic potential, i.e. with an improved lipid profile effect on top of the normalization of glucose- and insulin-levels (Keller and Wahli: Trends Endocrin. Metab. 1993; 4:291–296, Macdonald and Lane: Current Biology Vol.5 pp.618–621 (1995)).

SUMMARY OF THE INVENTION

The present invention provides indolyl derivatives useful as insulin sensitizers, particularly PPAR activators.

The invention is concerned especially with compounds of formula I

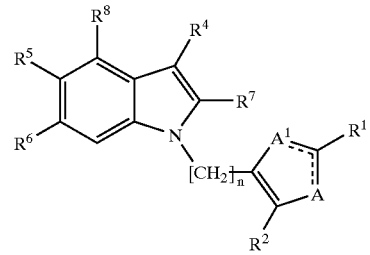

(I)

wherein

R¹ is aryl or heteroaryl;
R² is hydrogen, alkyl or cycloalkyl;
R³ is aryloxy, alkenyloxy, alkoxy or alkoxy substituted with one to three halogen atoms;
R⁴ is hydrogen, alkyl or cycloalkyl;
wherein any one of R⁵ and R⁶ is

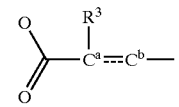

and the other is hydrogen, alkyl or cycloalkyl and, wherein the bond between the carbon atoms $C^a$ and $C^b$ is a carbon carbon single or double bond;
R⁷ is hydrogen, alkyl or cycloalkyl;
R⁸ is hydrogen, alkyl or cycloalkyl;
wherein any one of A and A¹ is nitrogen and the other is oxygen or sulfur;
n is 1, 2 or 3;

and pharmaceutically acceptable salts and esters thereof.

The compounds of formula I and their pharmaceutically acceptable salts and esters are useful as insulin sensitizers, particularly PPAR activators.

DETAILED DESCRIPTION OF THE INVENTION

The novel compounds of the present invention exceed the compounds known in the art, inasmuch as the), bind to and activate both, PPARα and PPARγ, simultaneously and very efficiently. Therefore, these compounds combine the antiglycemic effect of PPARγ activation with the anti-dyslipidemic effect of PPARα activation. Consequently, plasma glucose and insulin are reduced (=insulin sensitization), triglycerides lowered and HDL cholesterol increased (=improved lipid profile). In addition, such compounds may also lower LDL cholesterol, decrease blood pressure and counteract inflammatory atherosclerosis. Since multiple facets of the T2D disease syndrome are addressed by PPARα and γ coagonists, they are expected to have an enhanced therapeutic potential compared to the compounds already known in the art.

Accordingly, the compounds of formula I can be used in the prophylaxis and/or treatment of diabetes, particularly non-insulin dependent diabetes mellitus, elevated blood pressure, increased lipid and cholesterol levels, atherosclerotic diseases or metabolic syndrome.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$–$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, 2-hydroxyethoxy, 2-methoxyethoxy preferably methoxy and ethoxy and most preferred methoxy.

The term "alkenyl" alone or in combination, signifies a straight-chain or branched-chain alkenyl group with 2 to 8 carbon atoms comprising a carbon carbon double bond, preferably a straight or branched-chain alkenyl group with 2 to 6 carbon atoms and particularly preferred a straight or branched-chain alkenyl group with 2 to 4 carbon atoms. Examples of straight-chain and branched $C_2$–$C_8$ alkenyl groups are ethenyl, propenyl, isopropenyl, butenyl, isobutenyl, the isomeric pentenyls, the isomeric hexenyls, the isomeric heptenyls and the isomeric octenyls.

The term "alkenyloxy" alone or in combination, signifies a group of the formula alkenyl-O—, wherein the term alkenyl is defined as before. Examples are ethenyloxy, propenyloxy, pentenyloxy and preferably butenyloxy.

The term "aryl", alone or in combination, signifies a phenyl or naphthyl group, preferably a phenyl group which optionally carries one or more substituents, preferably one to three, each independently selected from e.g. halogen, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl substituted with one to three halogen atoms, e.g. trifluoromethyl; such as phenyl, fluorophenyl, chlorophenyl, methoxyphenyl, isopropoxyphenyl, ethylphenyl, isopropylphenyl, tert-butylphenyl, phenyl substituted with trifluoromethyl, phenyl substituted with two methyl groups, phenyl substituted with two methoxy groups, phenyl substituted with two fluoro atoms, phenyl substituted with two chloro atoms, phenyl substituted with methyl and fluoro or phenyl substituted with three methoxy groups.

The term "aryloxy" alone or in combination, signifies an aryl-O— group, wherein the term aryl is defined as before. A preferred example is phenyloxy.

The term "aralkyl", alone or in combination, signifies an alkyl or cycloalkyl group as previously defined in which one or more, preferably one hydrogen atom has been replaced by an aryl group as previously defined. Preferred are benzyl, benzyl substituted with hydroxy, alkoxy or halogen, preferably fluorine. Particularly preferred is benzyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring. The amino maybe, for example, —$NH_2$, methylamino, ethylamino, dimethylamino, diethylamino, methyl-ethylamino, pyrrolidin-1-yl or piperidino, etc., preferably amino, dimethylamino and diethylamino, and particularly primary amino.

The term "halogen" alone or in combination signifies fluorine, chlorine, bromine or iodine and preferably fluorine, chlorine or bromine.

The term "carbonyl", alone or in combination signifies the —C(O)— group.

The term "cyano", alone or in combination signifies the group —CN.

The term "heteroaryl", alone or in combination, signifies aromatic 5- to 10-membered heterocycle which contains one or more, preferably one or two hetero atoms selected from nitrogen, oxygen and sulfur, wherein sulfur are preferred. If desired, it can be substituted on one or more carbon atoms by halogen, alkyl, alkoxy, cyano, haloalkyl and/or trifluoromethyl. Preferred heteroaryl cycles are pyridinyl or thiophen-2-yl optionally substituted by one or more, preferably one or two substituents independently selected from halogen, alkyl, alkoxy, cyano, haloalkyl and trifluoromethyl. Particularly preferred is thiophen-2-yl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, or organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the sodium salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Further preferred pharmaceutically acceptable esters are alkyl, hydroxy-alkyl, alkoxy-alkyl, amino-alkyl, mono- or di-alkyl-amino-alkyl, morpholino-alkyl, pyrrolidino-alkyl, piperidino-alkyl, piperazino-alkyl, alkyl-piperazino-alkyl and aralkyl esters.

Additionally, any physiologically acceptable equivalents of the compounds of general formula (I), similar to the metabolically labile esters, which are capable of producing the parent compounds of general formula (I) in vivo, are within the scope of this invention.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123.

Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryle sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

Preferred are the compounds of formula I and pharmaceutically acceptable salts thereof, particularly the compounds of formula I.

Further preferred are compounds of formula I, wherein $R^3$ is alkoxy or alkoxy substituted with one to three halogen atoms;

$R^5$ is

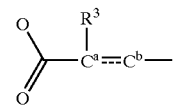

wherein the bond between the carbon atoms $C^a$ and $C^b$ is a carbon carbon single or double bond;

$R^6$ is hydrogen;
$R^7$ is hydrogen;
$R^8$ is hydrogen;
A is oxygen or sulfur; and
$A^1$ is nitrogen.

Further preferred are compounds according to formula I, wherein $R^1$ is thiophenyl or phenyl both optionally substituted with one to three, preferably one or two substituents independently selected from halogen, alkoxy, alkyl and alkyl substituted with one to three halogen atoms. Preferred are the above compounds of formula I, wherein thiophenyl is thiophen-2-yl.

Particularly preferred are those compounds according to formula I, wherein $R^1$ is thiophenyl, phenyl or phenyl substituted with one to three, preferably one or two substituents independently selected from fluoro, chloro, methoxy, ethoxy, propyloxy, isopropyloxy, methyl, ethyl, propyl, isopropyl, tert.-butyl, and trifluoromethyl. Preferred are the above compounds of formula I, wherein thiophenyl is thiophen-2-yl.

Another preferred embodiment of the present invention are the compounds of formula I, wherein $R^2$ is hydrogen, methyl or ethyl, preferably hydrogen or methyl. Particularly preferred are those compounds of formula I, wherein $R^2$ is methyl.

Preferred are compounds of formula I, wherein $R^3$ is methoxy, ethoxy, propyloxy, isopropyloxy, phenoxy or butenyloxy.

Also preferred are the compounds of formula I, wherein $R^3$ is methoxy or ethoxy. Particularly preferred are those compounds, wherein $R^1$ is ethoxy.

Further preferred are compounds of formula I, wherein $R^4$ is methyl.

Another preferred aspect of the present invention are the compounds of formula I, wherein $R^4$ is hydrogen.

Preferred are compound of formula I, wherein $R^6$ is

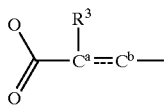

and $R^5$ is hydrogen, alkyl or cycloalkyl and, wherein the bond between the carbon atoms $C^a$ and $C^b$ is a carbon carbon double bond, preferably a carbon carbon single bond.

Particularly preferred are compound of formula I, wherein $R^5$ is

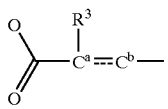

and $R^6$ is hydrogen, alkyl or cycloalkyl and, wherein the bond between the carbon atoms $C^a$ and $C^b$ is a carbon carbon double bond, preferably a carbon carbon single bond.

Also preferred are compounds according to formula I, wherein $R^6$ is hydrogen.

Further preferred are the compounds according to formula I, wherein $R^7$ is hydrogen.

Another preferred aspect of the present invention are the compounds of formula I, wherein $R^7$ is methyl.

Further preferred are the compounds of formula I, wherein $R^8$ is hydrogen.

Another preferred aspect of the invention are the compounds according to formula I, wherein $R^8$ is methyl.

Preferred are compounds of formula I, wherein n is 1, 2 or 3. Further preferred are those compounds of formula I, wherein n is 1 or 2. Particularly preferred are those, wherein n is 1.

Also preferred are the compounds of formula I, wherein A is sulfur. Particularly preferred compounds of formula I are those, wherein A is oxygen.

Preferred are the compounds according to formula I, wherein A is nitrogen and $A^1$ is oxygen. These compounds have the following formula:

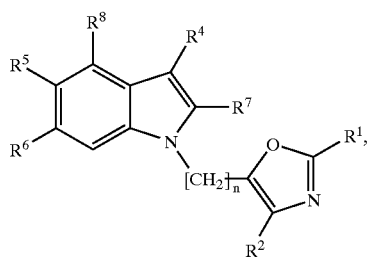

wherein $R^1$ to $R^8$ and n are defined as before.

Preferred are the compounds according to formula I, wherein A is nitrogen and $A^1$ is sulfur. These compounds have the following formula:

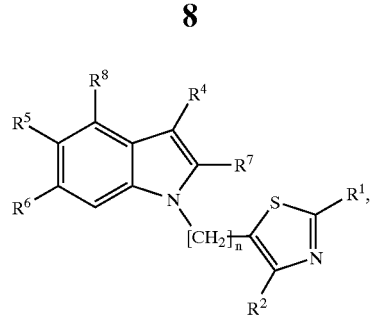

wherein $R^1$ to $R^8$ and n are defined as before.

Further preferred are the compounds according to formula I, wherein $A^1$ is nitrogen and A is oxygen. These compounds have the following formula:

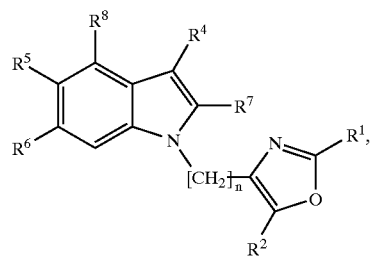

wherein $R^1$ to $R^8$ and n are defined as before.

Further preferred are the compounds according to formula I, wherein $A^1$ is nitrogen and A is sulfur. These compounds have the following formula:

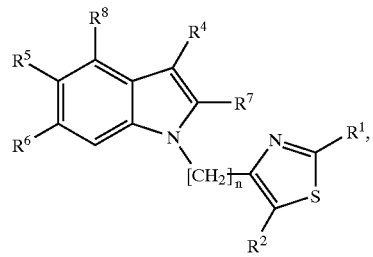

wherein $R^1$ to $R^8$ and n are defined as before.

The compounds of formula I can contain several asymmetric centres and can be present in the form of optically pure enantiomers, mixtures of enantiomers such as, for example racemates, optically pure diastereoisomers, mixtures of diastereoisomers, diastereo-isomeric racemates or mixtures of diastereoisomeric racemates. The optically active forms can be obtained for example by resolution of the racemates, by asymmetric synthesis or asymmetric chromatography (chromatography with a chiral adsorbens or eluant).

The term "asymmetric carbon atom" means a carbon atom with four different substituents. According to the Cahn-Ingold-Prelog-Convention the asymmetric carbon atom can be of the "R" or "S" configuration.

Preferred are chiral compounds of formula (I), wherein any one of $R^5$ and $R^6$, preferably $R^5$ is

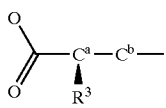

and the other is hydrogen, alkyl or cycloalkyl and the asymmetric carbon atom $C^a$ is of the R configuration.

Particularly preferred are chiral compounds of formula (I), wherein anyone of $R^5$ and $R^6$, preferably $R^5$ is

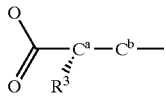

and the other is hydrogen, alkyl or cycloalkyl and the asymmetric carbon atom $C^a$ is of the S configuration.

Preferred are compounds according to the following formula (Ie)

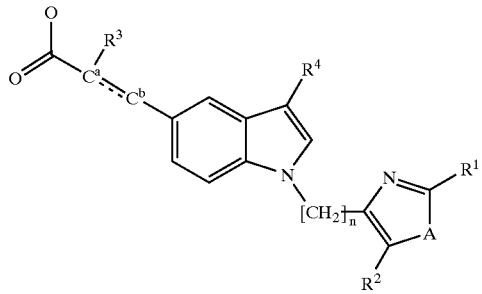

and pharmaceutically acceptable salts and esters thereof, wherein $R^1$ is aryl or heteroaryl;
$R^2$ is hydrogen, alkyl or cycloalkyl;
$R^3$ is alkoxy or alkoxy substituted with one to three halogen atoms;
$R^4$ is hydrogen, alkyl or cycloalkyl;
A is oxygen or sulfur;
n is 1, 2 or 3;

and, wherein the bond between the carbon atoms $C^a$ and $C^b$ is a carbon carbon single or double bond.

Further preferred are those compounds of formula Ie, wherein the bond between the carbon atoms $C^a$ and $C^b$ is a carbon carbon double bond. These compounds have the following formula Ia

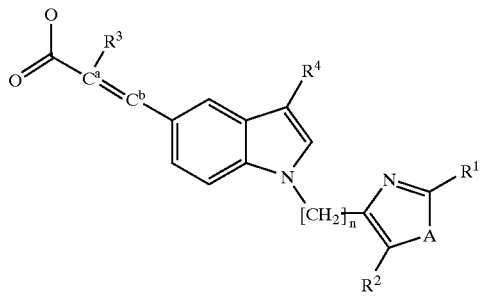

wherein $R^1$ to $R^4$, A and n are defined as before.

Particularly preferred are those compounds of formula Ie, wherein the bond between the carbon atoms $C^a$ and $C^b$ is a carbon carbon single bond. These compounds have the following formula Ib

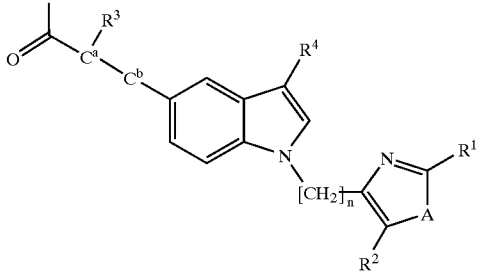

wherein $R^1$ to $R^4$, A and n are defined as before.

Preferred are chiral compounds of formula (Ic),

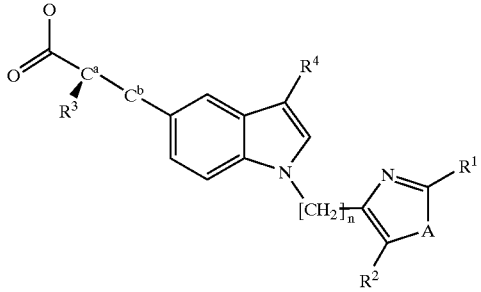

wherein $R^1$ to $R^4$, A and n are defined as before and the asymmetric carbon atom $C^a$ is of the R configuration.

Particularly preferred are chiral compounds of formula (Id),

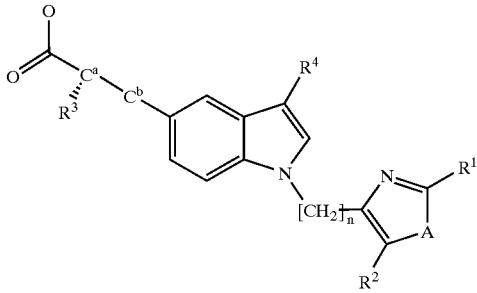

wherein $R^1$ to $R^4$, A and n are defined as before and the asymmetric carbon atom $C^a$ is of the S configuration.

Examples of preferred compounds of formula (I) are (rac)-2-Ethoxy-3-[1-(5-methyl-2-phenyl-oxazol-4-ylmethyl)-1H-indol-5-yl]-propionic acid;
(S)-2-Ethoxy-3-[1-(5-methyl-2-phenyl-oxazol-4-ylmethyl)-1H-indol-5-yl]-propionic acid;
(rac)-2-Ethoxy-3-{1-[2-(2-fluoro-phenyl)-5-methyl-oxazol-4-ylmethyl]-1H-indol-5-yl}-propionic acid;
(rac)-3-{1-[2-(2-Chloro-phenyl)-5-methyl-oxazol-4-ylmethyl]-1H-indol-5-yl}-2-ethoxy-propionic acid;
(S)-3-{1-[2-(2-Chloro-phenyl)-5-methyl-oxazol-4-ylmethyl]-1H-indol-5-yl}-2-ethoxy-propionic acid;
(rac)-2-Ethoxy-3-[1-(5-methyl-2-o-tolyl-oxazol-4-ylmethyl)-1H-indol-5-yl]-propionic acid;
(rac)-2-Ethoxy-3-{1-[2-(2-methoxy-phenyl)-5-methyl-oxazol-4-ylmethyl]-1H-indol-5-yl}-propionic acid;

(S)-2-Ethoxy-3-{1-[2-(2-methoxy-phenyl)-5-methyl-oxazol-4-ylmethyl]-1H-indol-5-yl}-propionic acid;
(rac)-2-Ethoxy-3-{1-[2-(2-isopropoxy-phenyl)-5-methyl-oxazol-4-ylmethyl]-1H-indol-5-yl}-propionic acid;
(rac)-3-{1-[2-(3-Chloro-phenyl)-5-methyl-oxazol-4-ylmethyl-1H-indol-5-yl}-2-ethoxy-propionic acid;
(rac)-2-Ethoxy-3-{1-[2-(4-ethyl-phenyl)-5-methyl-oxazol-4-ylmethyl]-1H-indol-5-yl}-propionic acid;
(S)-2-Ethoxy-3-{1-[2-(4-ethyl-phenyl)-5-methyl-oxazol-4-ylmethyl]-1H-indol-5-yl}-propionic acid;
(R)-2-Ethoxy-3-{1-[2-(4-ethyl-phenyl)-5-methyl-oxazol-4-ylmethyl]-1H-indol-5-yl}-propionic acid;
(rac)-2-Ethoxy-3-{1-[2-(4-isopropyl-phenyl)-5-methyl-oxazol-4-ylmethyl]-1H-indol-5-yl}-propionic acid;
(rac)-3-{1-[2-(4-tert-Butyl-phenyl)-5-methyl-oxazol-4-ylmethyl]-1H-indol-5-yl}-2-ethoxy-propionic acid;
(rac)-2-Ethoxy-3-{1-[2-(4-fluoro-phenyl)-5-methyl-oxazol-4-ylmethyl]-1H-indol-5-yl}-propionic acid;
(rac)-2-Ethoxy-3-{1-[5-methyl-2-(4-trifluoromethyl-phenyl)-oxazol-4-ylmethyl]-1H-indol-5-yl}-propionic acid;
(S)-2-Ethoxy-3-{1-[5-methyl-2-(4-trifluoromethyl-phenyl)-oxazol-4-ylmethyl]-1H-indol-5-yl}-propionic acid;
(rac)-3-{1-[2-(3,5-Dimethyl-phenyl)-5-methyl-oxazol-4-ylmethyl]-1H-indol-5-yl}-2-ethoxy-propionic acid;
(rac)-3-{1-[2-(3,5-Dimethoxy-phenyl)-5-methyl-oxazol-4-ylmethyl]-1H-indol-5-yl}-2-ethoxy-propionic acid;
(S)-3-{1-[2-(3,5-Dimethoxy-phenyl)-5-methyl-oxazol-4-ylmethyl]-1H-indol-5-yl}-2-ethoxy-propionic acid;
(rac)-3-{1-[2-(3,5-Difluoro-phenyl)-5-methyl-oxazol-4-ylmethyl]-1H-indol-5-yl}-2-ethoxy-propionic acid;
(rac)-3-{1-[2-(3,5-Dichloro-phenyl)-5-methyl-oxazol-4-ylmethyl]-1H-indol-5-yl}-2-ethoxy-propionic acid;
(rac)-2-Ethoxy-3-{1-[2-(4-fluoro-3-methyl-phenyl)-5-methyl-oxazol-4-ylmethyl)-1H-indol-5-yl}-propionic acid;
(S)-2-Ethoxy-3-{1-[2-(4-fluoro-3-methyl-phenyl)-5-methyl-oxazol-4-ylmethyl]-1H-indol-5-yl}-propionic acid;
(rac)-2-Ethoxy-3-[1-(5-methyl-2-thiophen-2-yl-oxazol-4-ylmethyl]-1H-indol-5-yl]-propionic acid;
(rac)-2-Ethoxy-3-{1-[2-(3,4,5-trimethoxy-phenyl)-5-methyl-oxazol-4-ylmethyl]-1H-indol-5-yl}-propionic acid;
(rac)-2-Ethoxy-3-[1-(2-phenyl-oxazol-4-ylmethyl)-1H-indol-5-yl]-propionic acid;
(rac)-2-Ethoxy-3-[1-(2-phenyl-thiazol-4-ylmethyl)-1H-indol-5-yl]-propionic acid;
rac-2-Ethoxy-3-[1-(5-methyl-2-phenyl-thiazol-4-ylmethyl)-1H-indol-5-yl]-propionic acid;
(rac)-3-{1-[2-(4-Chloro-phenyl)-thiazol-4-ylmethyl]-1H-indol-5-yl}-2-ethoxy-propionic acid;
(Z)-2-Methoxy-3-[1-(5-methyl-2-phenyl-oxazol-4-ylmethyl)-1H-indol-5-yl]-acrylic acid;
(rac)-2-Methoxy-3-[1-(5-methyl-2-phenyl-oxazol-4-ylmethyl)-1H-indol-5-yl]-propionic acid;
(Z)-2-Methoxy-3-{1-[2-(5-methyl-2-phenyl-oxazol-4-yl)-ethyl]-1H-indol-5-yl}-acrylic acid;
(rac)-2-Methoxy-3-{1-[2-(5-methyl-2-phenyl-oxazol-4-yl)-ethyl]-1H-indol-5-yl}-propionic acid;
rac-2-Ethoxy-3-{1-[2-(4-isopropyl-phenyl)-5-methyl-oxazol-4-ylmethyl]-3-methyl-1H-indol-5-yl}-propionic acid;
rac-2-Ethoxy-3-{3-methyl-1-[5-methyl-2-(4-trifluoromethyl-phenyl)-oxazol-4-ylmethyl]-1H-indol-5-yl}-propionic acid;
rac-3-{1-[2-(2-Chloro-phenyl)-5-methyl-oxazol-4-ylmethyl]-3-methyl-1H-indol-5-yl}-2-ethoxy-propionic acid;
rac-2-Ethoxy-3-1-[2-(4-fluoro-3-methyl-phenyl)-5-methyl-oxazol-4-ylmethyl]-3-methyl-1H-indol-5-yl]-propionic acid;
rac-2-Ethoxy-3-{2-methyl-1-[5-methyl-2-(4-trifluoromethyl-phenyl)-oxazol-4-ylmethyl]-1H-indol-5-yl}-propionic acid;
rac-2-Ethoxy-3-{1-[2-(4-isopropyl-phenyl)-5-methyl-oxazol-4-ylmethyl]-2-methyl-1H-indol-5-yl}-propionic acid;
rac-2-Ethoxy-3-{1-[2-(4-fluoro-3-methyl-phenyl)-5-methyl-oxazol-4-ylmethyl]-2-methyl-1H-indol-5-yl}-propionic acid;
rac-3-{1-[2-(2-Chloro-phenyl)-5-methyl-oxazol-4-ylmethyl]-2-methyl-1H-indol-5-yl}-2-ethoxy-propionic acid;
rac-2-Ethoxy-3-[2-methyl-1-(2-phenyl-thiazol-4-ylmethyl)-1H-indol-5-yl]-propionic acid;
rac-3-{1-[2-(4-tert-Butyl-phenyl)-oxazol-4-ylmethyl]-2-methyl-1H-indol-5-yl}-2-ethoxy-propionic acid;
rac-3-[1-(5-Methyl-2-o-tolyl-oxazol-4-ylmethyl)-1H-indol-5-yl]-2-propoxy-propionic acid;
rac-3-{1-[2-(2-Methoxy-phenyl)-5-methyl-oxazol-4-ylmethyl]-1H-indol-5-yl}-2-propoxy-propionic acid;
rac-3-{1-[5-Methyl-2-(4-trifluoromethyl-phenyl)-oxazol-4-ylmethyl]-1H-indol-5-yl}-2-propoxy-propionic acid;
rac-3-{1-[5-Methyl-2-(4-trifluoromethyl-phenyl)-oxazol-4-ylmethyl]-1H-indol-5-yl}-2-phenoxy-propionic acid;
rac-3-{1-[2-(4-Isopropyl-phenyl)-5-methyl-oxazol-4-ylmethyl]-1H-indol-5-yl}-2-phenoxy-propionic acid;
rac-3-{1-[2-(2-Chloro-phenyl)-5-methyl-oxazol-4-ylmethyl]-1H-indol-5-yl}-2-phenoxy-propionic acid;
rac-3-{1-[2-(4-Fluoro-3-methyl-phenyl)-5-methyl-oxazol-4-ylmethyl]-1H-indol-5-yl}-2-phenoxy-propionic acid;
rac-2-Isopropoxy-3-[1-(5-methyl-2-o-tolyl-oxazol-4-ylmethyl)-1H-indol-5-yl]-propionic acid;
rac-2-Isopropoxy-3-{1-[2-(2-methoxy-phenyl)-5-methyl-oxazol-4-ylmethyl]-1H-indol-5-yl}-propionic acid;
rac-3-{1-[2-(2-Chloro-phenyl)-5-methyl-oxazol-4-ylmethyl]-1H-indol-5-yl}-2-isopropoxy-propionic acid;
rac-2-Isopropoxy-3-{1-[5-methyl-2-(4-trifluoromethyl-phenyl)-oxazol-4-ylmethyl]-1H-indol-5-yl}-propionic acid;
rac-2-But-3-enyloxy-3-[1-(5-methyl-2-o-tolyl-oxazol-4-ylmethyl)-1H-indol-5-yl]-propionic acid;
rac-2-But-3-enyloxy-3-{1-[2-(2-methoxy-phenyl)-5-methyl-oxazol-4-ylmethyl]-1H-indol-5-yl}-propionic acid;
rac-2-But-3-enyloxy-3-{1-[2-(2-chloro-phenyl)-5-methyl-oxazol-4-ylmethyl]-1H-indol-5-yl}-propionic acid;
rac-2-But-3-enyloxy-3-{1-[5-methyl-2-(4-trifluoromethyl-phenyl)-oxazol-4-ylmethyl]-1H-indol-5-yl}-propionic acid;
rac-2-Ethoxy-3-{2-methyl-1-[2-(5-methyl-2-phenyl-oxazol-4-yl)-ethyl]-1H-indol-5-yl}-propionic acid;
rac-2-Ethoxy-3-{2-methyl-1-[3-(5-methyl-2-phenyl-oxazol-4-yl)-propyl]-1H-indol-5-yl}-propionic acid;
rac-2-Ethoxy-3-{4-methyl-1-[5-methyl-2-(4-trifluoromethyl-phenyl)-oxazol-4-ylmethyl]-1H-indol-5-yl}-propionic acid;
rac-2-Ethoxy-3-{1-[2-(4-isopropyl-phenyl)-5-methyl-oxazol-4-ylmethyl]-4-methyl-1H-indol-5-yl}-propionic acid;
rac-2-Ethoxy-3-{1-[2-(4-fluoro-3-methyl-phenyl)-5-methyl-oxazol-4-ylmethyl]-4-methyl-1H-indol-5-yl}-propionic acid;
rac-3-{1-[2-(2-Chloro-phenyl)-5-methyl-oxazol-4-ylmethyl]-4-methyl-1H-indol-5-yl}-2-ethoxy-propionic acid;

rac-3-{1-[2-(3,5-Dimethoxy-phenyl)-5-methyl-oxazol-4-ylmethyl]-4-methyl-1H-indol-5-yl}-2-ethoxy-propionic acid;
rac-2-Ethoxy-3-{1-[4-methyl-2-(4-trifluoromethyl-phenyl)-thiazol-5-ylmethyl]-1H-indol-5-yl}-propionic acid;
(Z)-3-{1-[2-(2-Chloro-phenyl)-5-methyl-oxazol-4-ylmethyl]-1H-indol-5-yl}-2-ethoxy-acrylic acid;
rac-2-Ethoxy-3-{1-[2-(4-isopropyl-phenyl)-5-methyl-oxazol-4-ylmethyl]-1H-indol-6-yl}-propionic acid;
rac-3-{1-[2-(3,5-Dimethoxy-phenyl)-5-methyl-oxazol-4-ylmethyl]-1H-indol-6-yl}-2-ethoxy-propionic acid and
rac-2-Ethoxy-3-{1-[2-(4-isopropyl-phenyl)-thiazol-4-ylmethyl]-1H-indol-6-yl}-propionic acid.

Examples of particularly preferred compounds of formula (I) are (S)-3-{1-[2-(2-Chloro-phenyl)-5-methyl-oxazol-4-ylmethyl]-1H-indol-5-yl}-2-ethoxy-propionic acid;
(S)-2-Ethoxy-3-{1-[2-(2-methoxy-phenyl)-5-methyl-oxazol-4-ylmethyl]-1H-indol-5-yl}-propionic acid;
(S)-2-Ethoxy-3-{1-[5-methyl-2-(4-trifluoromethyl-phenyl)-oxazol-4-ylmethyl]-1H-indol-5-yl}-propionic acid;
(S)-3-{1-[2-(3,5-Dimethoxy-phenyl)-5-methyl-oxazol-4-ylmethyl]-1H-indol-5-yl}-2-ethoxy-propionic acid; and
(S)-2-Ethoxy-3-{1-[2-(4-fluoro-3-methyl-phenyl)-5-methyl-oxazol-4-ylmethyl]-1H-indol-5-yl}-propionic acid.

Examples of particularly preferred compounds of formula (I) are (S)-3-{1-[2-(2-Chloro-phenyl)-5-methyl-oxazol-4-ylmethyl]-1H-indol-5-yl}-2-ethoxy-propionic acid;
(S)-2-Ethoxy-3-{1-[2-(2-methoxy-phenyl)-5-methyl-oxazol-4-ylmethyl]-1H-indol-5-yl}-propionic acid;
(S)-2-Ethoxy-3-{1-[5-methyl-2-(4-trifluoromethyl-phenyl)-oxazol-4-ylmethyl]-1H-indol-5-yl}-propionic acid;
(S)-3-{1-[2-(3,5-Dimethoxy-phenyl)-5-methyl-oxazol-4-ylmethyl]-1H-indol-5-yl}-2-ethoxy-propionic acid;
(S)-2-Ethoxy-3-{1-[2-(4-fluoro-3-methyl-phenyl)-5-methyl-oxazol-4-ylmethyl]-1H-indol-5-yl}-propionic acid;
rac-2-Ethoxy-3-{3-methyl-1-[5-methyl-2-(4-trifluoromethyl-phenyl)-oxazol-4-ylmethyl]-1H-indol-5-yl}-propionic acid;
rac-3-{1-[2-(2-Chloro-phenyl)-5-methyl-oxazol-4-ylmethyl]-3-methyl-1H-indol-5-yl}-2-ethoxy-propionic acid;
rac-2-Ethoxy-3-{1-[2-(4-fluoro-3-methyl-phenyl)-5-methyl-oxazol-4-ylmethyl]-3-methyl-1H-indol-5-yl}-propionic acid;
rac-3-{1-[5-Methyl-2-(4-trifluoromethyl-phenyl)-oxazol-4-ylmethyl]-1H-indol-5-yl}-2-propoxy-propionic acid;
rac-2-Isopropoxy-3-{1-[5-methyl-2-(4-trifluoromethyl-phenyl)-oxazol-4-ylmethyl]-1H-indol-5-yl}-propionic acid;
rac-2-But-3-enyloxy-3-{1-[5-methyl-2-(4-trifluoromethyl-phenyl)-oxazol-4-ylmethyl]-1H-indol-5-yl}-propionic acid; and
rac-2-Ethoxy-3-{1-[2-(4-isopropyl-phenyl)-5-methyl-oxazol-4-ylmethyl]-4-methyl-1H-indol-5-yl}-propionic acid.

Preferred is the compound (S)-3-{1-[2-(2-chloro-phenyl)-5-methyl-oxazol-4-ylmethyl]-1H-indol-5-yl}-2-ethoxy-propionic acid and pharmaceutically acceptable salts and esters thereof. Particularly preferred is the compound (S)-3-{1-[2-(2-chloro-phenyl)-5-methyl-oxazol-4-ylmethyl]-1H-indol-5-yl}-2-ethoxy-propionic acid.

Processes for the manufacture of compounds of formula I are an object of the invention.

The substituents and indices used in the following description of the processes have the significance given above unless indicated to the contrary.

Compounds of general formula (I), particularly compounds according to formula (If) or (Ig), wherein $R^1$ to $R^8$, A, $A^1$ and n are defined as before can be prepared according to Scheme I.

Scheme I

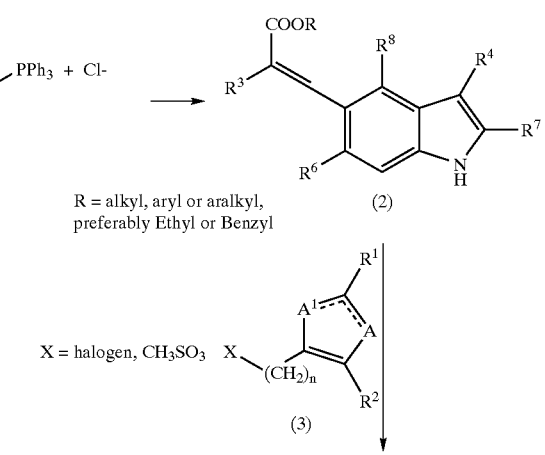

R = alkyl, aryl or aralkyl, preferably Ethyl or Benzyl

X = halogen, $CH_3SO_3$

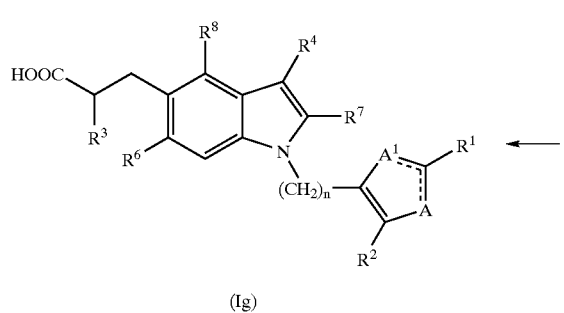

(Ig)

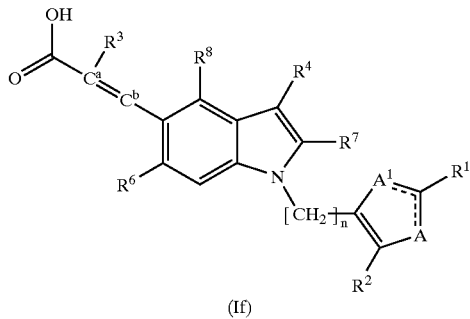

(If)

An analogous reaction scheme with the same reaction sequences applies for the isomeric compound series leading to compounds of general formula (I), particularly compounds according to formula (Ih) or (Ii), Alternatively, compounds of general formula (Ig), wherein $R^1$ to $R^8$, A, $A^1$ and n are defined as before can be prepared according to Scheme II:

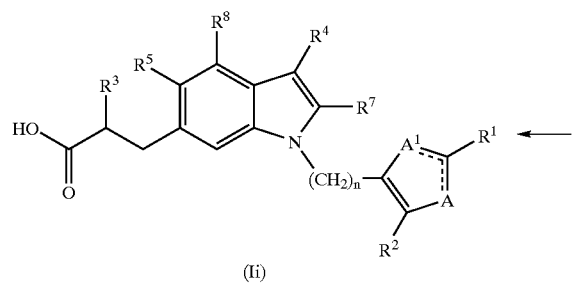

(Ii)

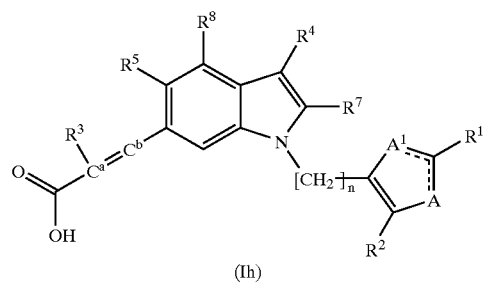

(Ih)

carrying the

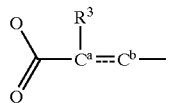

substituent at the indole 6 position.

Aldehydes (1) can be reacted with a Wittig salt [as e.g. described in Tetrahedron (1994), 50(25), 7543–56] such as (1,2-diethoxy-2-oxoethyl)-triphenyl-phosphonium chloride or (1-methoxy-2-benzyloxy-oxoethyl)-triphenyl-phosphonium chloride in solvents like isopropanol, dichloromethane or tetrahydrofuran or mixtures thereof in the presence of a base like potassium carbonate or tetramethyl guanidine, preferably between 0° C. and the reflux temperature of the solvents, giving acrylic esters (2) as E and/or Z isomers. N-Alkylation of indoles (2) with the heterocycles (3) can be accomplished in a solvent like N,N-dimethylformamide or N-methly-pyrrolidone in the presence of a base like sodium hydride or potassium tert-butylate, preferable between 0° C. and room temperature followed by hydrolysis of the ester function, preferably with LiOH or NaOH in solvent mixtures like dioxane/water, tetrahydrofuran or ethanol/water preferable between 0° C. and room temperature leading to acrylic acids (If). Alternatively, in situ formation of the acrylic acids (If) can be accomplished by treatment of indoles (2) with the heterocycles (3) in the presence of KOH in DMSO between 0° C. and 80° C. preferably at 22° C.

Catalytic hydrogenation of compounds (If) with palladium on charcoal in solvents like methanol, ethanol, dichloromethane or tetrahydrofuran or mixtures thereof leads to the indole propionic acids (Ig).

Scheme II

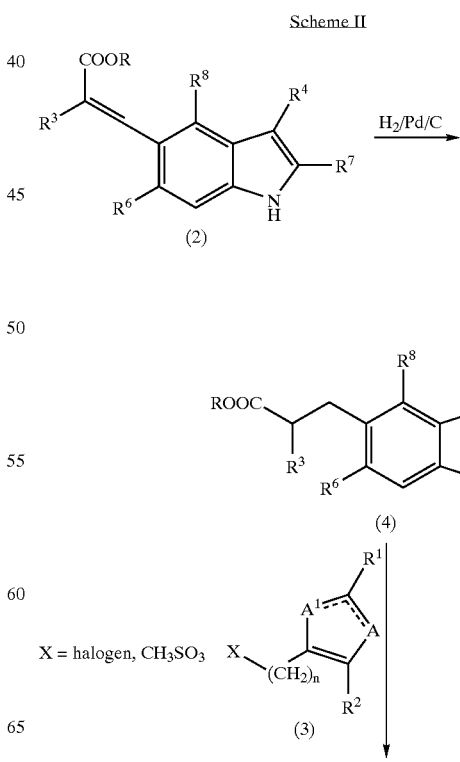

-continued

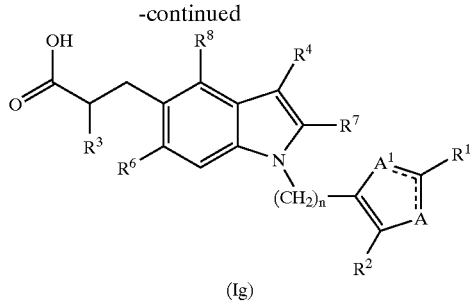

(Ig)

An analogous reaction scheme with the same reaction sequences applies for the isomeric compound series leading to compounds of general formula (I), particularly compounds according to formula (Ii),

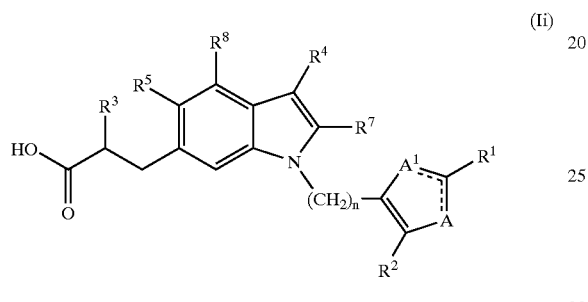

(Ii)

carrying the

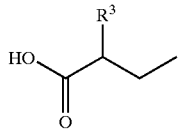

substituent at the indole 6 position.

The alternative preparation of (Ig) according to Scheme II, preferentially be used when $R^3$, $R^4$, $R^5$, $R^6$, $R^7$ and $R^8$ are fixed and $R^1$, $R^2$ and A, $A^1$ and n are varied and when homochiral compounds are synthesized, follows the same type of reactions as described in Scheme I. In addition, in situ formation of compounds (Ig) can be performed by treating a mixture of indoles (4) and heterocycles (3) with an excess amount of sodium hydride in a solvent like N,N-dimethylformamide between 0° C. and room temperature leading directly to acids (Ig). Homochiral acids (Ig) can be prepared by preparation of optically pure or optically enriched intermediates (e.g. by enzymatic resolution of the racemic esters (4) using e.g. a Lipase, the resolved acid being esterified after separation) and further transformation of such optically pure or optically enriched esters (4) into optically pure or optically enriched acids (Ig). Alternatively, racemic or optically enriched acids (Ig) can be separated into their antipodes by methods known in the art, such as separation of the antipodes via diastereomeric salts by crystallization with optically pure amines such as e.g. (R) or (S)-1-phenyl-ethylamine, (1R) or (S)-1-naphthalen-1-yl-ethylamine, brucine, quinine or quinidine or by separation of the antipodes by specific chromatographic methods using either a chiral adsorbens or a chiral eluent.

Compounds of general formula (I), particularly compounds wherein $R^3$ is varied, can be prepared according to Scheme III:

Scheme III

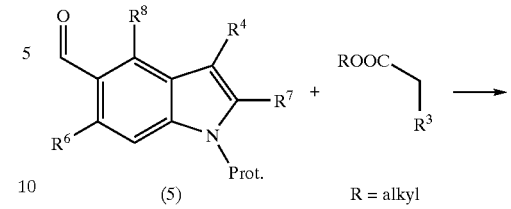

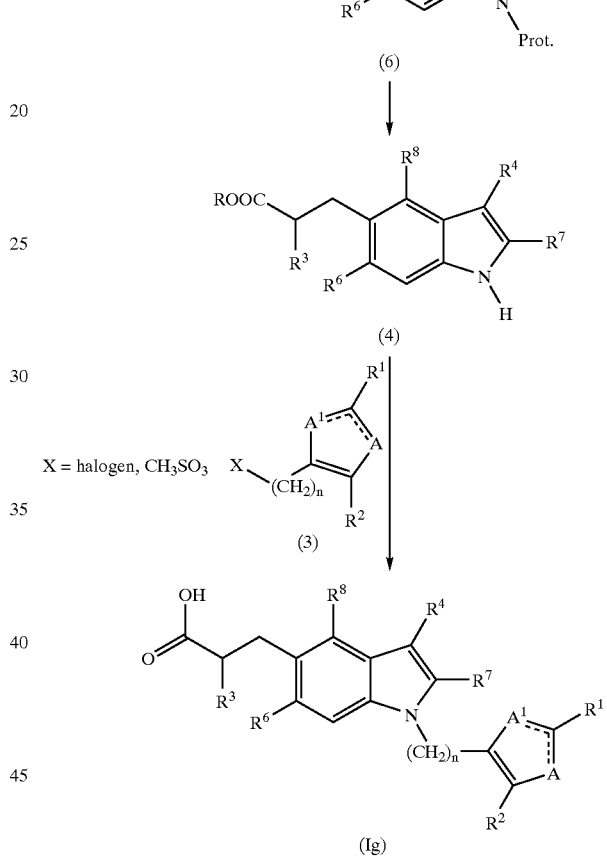

An analogous reaction scheme with the same reaction sequences applies for the isomeric compound series leading to compounds of general formula (I), particularly compounds according to formula (Ii),

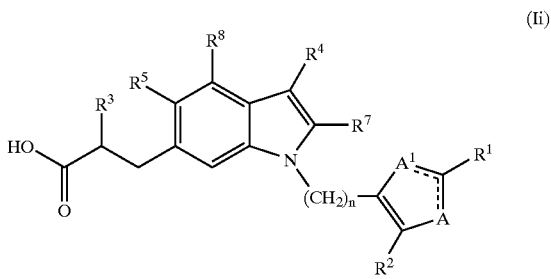

(Ii)

-continued

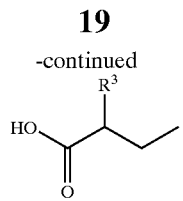

Carrying the substituent at the indole 6 position.

Formyl indoles (5) carrying a suitable protective function (Prot.) at the indole nitrogen group, e.g. a 2-trimethylsilanyl-ethoxymethyl (SEM)-group or a benzenesulfonyl group can react with enolates of alkoxy-, alkenyloxy or aryloxy-acetic acid esters (preferably prepared at −78° C. in a solvent like tetrahydrofuran with a base like lithium diisopropylamide) at low temperature to give aldol compounds (6) as mixtures of diastereomeric racemates. Compounds (6) can be transformed into indole propionic acids (4) by different synthetic routes depending on the protective group used and the nature of $R^3$. If $R^3$ contains a double bond and if a benzenesulfonyl group is used as indole protective function, then, the following two step procedure is preferably used: i) elimination of water by treatment with para-toluenesulfonic acid in a solvent like benzene preferably at reflux; ii) reaction with magnesium in methanol at reflux to simultaneously reduce the double bond and remove the protective function. If $R^3$ does not contain a double bond, and if a 2-trimethylsilanyl-ethoxymethyl (SEM)-group is used as indole protective function, then, the following five step procedure is preferably used: i) treatment with methanesulfonyl chloride in a solvent like dichloromethane followed by treatment with e.g. 1,8-diazabicyclo[5.4.0.]undec-7-ene(1,5,5) in a solvent like tetrahydrofuran preferably at elevated temperature to give the unsaturated ester compounds as mixtures of E and/or Z isomers; ii) hydrogenation of the double bond with e.g. palladium on charcoal in a solvent like ethanol; iii) saponification of the ester function using standard conditions; iv) removal of the protective function with e.g. tetra-butylammonium fluoride (as solution in tetrahydrofuran) in a solvent like N,N-dimethylformamide in the presence of ethylene diamine in a preferred temperature range between 50° C. and 80° C.; v) re-esterification using e.g. methyliodide, sodium hydrogen carbonate in N,N-dimethylformamide. The transformation of compounds (4) into compounds (Ig) by condensation with heterocycles (3) can then be performed as outlined in Schemes I and II.

5-Formyl indoles (1), wherein $R^6$ represents hydrogen, alkyl or cycloalkyl, or the corresponding 6-formyl analoges, wherein $R^5$ represents hydrogen, alkyl or cycloalkyl, used as starting materials in Scheme I, are known or can be synthesized by methods known in the art. Selected synthetic approaches to 5-formyl indoles (1), which are also applicable for the synthesis of 6-formyl indoles, are depicted in Scheme IV.

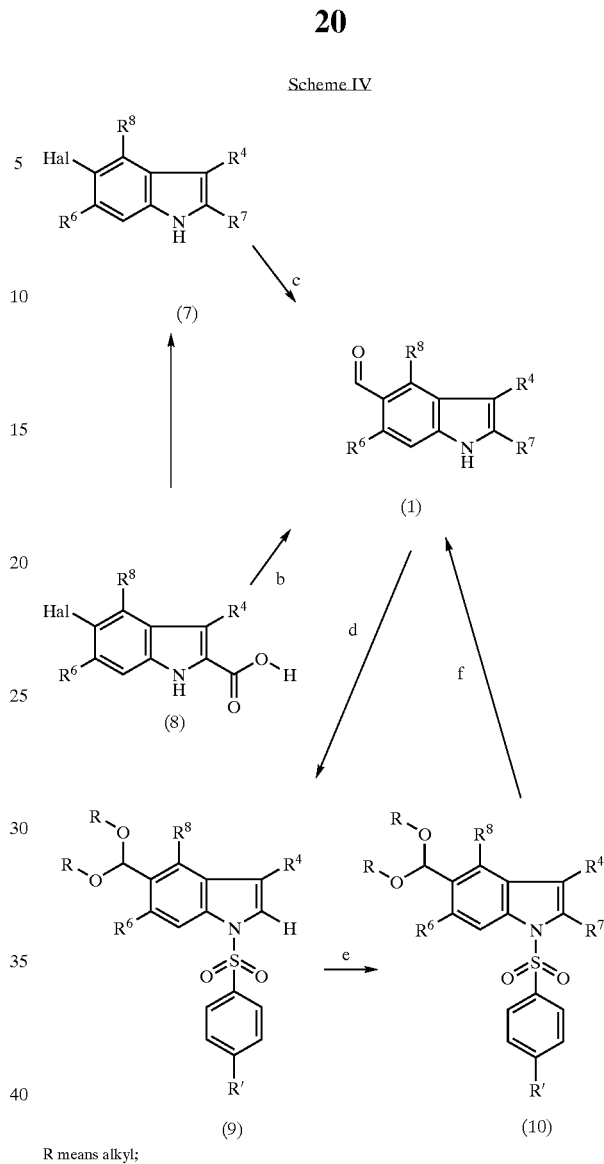

R means alkyl;
R' means hydrogen or alkyl;

The conversion of halogen indoles (7) into formyl indoles (1) can be performed e.g. by treatment of the corresponding bromo- or iodo-indoles with an alkyl lithium reagent, e.g. n-butyl lithium, in a solvent like tetrahydrofuran preferably at −78° C. followed by treatment with N,N-dimethylformamide or by carbonylation of halogen indoles (7) with carbon monoxide at pressures up to 30 to 50 bar in solvents like toluene or benzene in the presence of a suitable catalyst (e.g. a palladium catalyst) at temperatures between room temperature and 200° C. [compare e.g. Angew Chem, Int Ed Engl 1989, 28 (10), 1386] (step c). Alternatively, formyl indoles (1) with can be prepared from halogen substituted indoles (7) or 2-carboxy halo indoles (8) by treatment with copper (I) cyanide in quinoline at temperatures between 200° C. and 270° C. (compare Liebigs Ann. Chem. 1975, 160–194) followed by reduction of the nitriles thus formed with sodium hypophosphite and Raney nickel preferably in a mixture of water, acetic acid and pyridine at temperatures ranging between room temperature and 60° C. [compare Helvetica Chimica Acta 51, 1616–1628 (1968)] (step b or c). Halogen substituted indoles (7) with $R^7$=H can optionally be prepared from 2-carboxy halo indoles (8) in a solvent like quinoline in the presence of a decarboxylation catalyst like copper powder at temperatures between 200° C. and 270° C. (step a). Formyl indoles (1) with $R^7$=H can be transformed into the corresponding analogues with $R^7$=alkyl by procedures as indicated in Scheme IV: i) introduction of a protective function at the indole nitrogen, e.g. a benzenesulfonyl group (e.g. using benzenesulfonyl chloride, tetrabutylammonium hydrogensulfate in toluene/50% aqueous sodium hydroxide); ii) protection of the aldehyde function, e. g. in form of a dialkyl acetal (step d); iii) introduction of the $R^7$ substituent by treatment first with e.g. tert-butyl lithium in a solvent like tetrahydrofuran at temperatures between −70° C. and room temperature followed by reaction with an alkyl halide at temperatures between −70° C. and room temperature (step e); iv) removal of the aldehyde protective function followed by reduction to the corresponding primary alcohol; v) removal of the indole protective function, e.g. removal of a benzenesulfonyl group with potassium hydroxide in methanol at elevated temperatures; vi) re-oxidation of the primary alcohol to an aldehyde function, e.g. using Swern conditions (oxalyl chloride/dimethylsulfoxide/triethylamine in dichloromethane, −78° C. to room temperature) (step f).

Possible syntheses of 2-carboxy halo indoles (8) are depicted in Schemes XII and XIII.

Starting compounds of formula (3), wherein A is oxygen and $A^1$ is nitrogen and n is 1 or 2 can be obtained e.g. according to Scheme V.

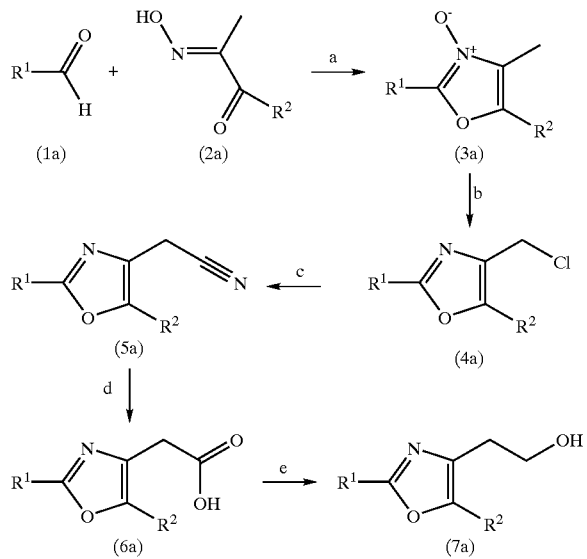

Scheme V

Aldehydes (1a) are commercially available or known. They are condensed with diketo-monoximes (2a) according to literature precedence (Goto, Y.; Yamazaki, M.; Hamana, M.; Chem Pharm Bull (1971), 19, 2050) in the presence of a strong acid, typically HCl, in a polar solvent like AcOH to yield the oxazole-N-oxides (3a) (step a). Subsequent treatment with $POCl_3$ in dichloromethane under reflux provides the corresponding primary chlorides (4a) (Goto, Y.; Yamazaki, M.; Hamana, M.; Chem Pharm Bull (1971), 19, 2050, step b). These intermediates are either used as such, transformed according to well established methods into the corresponding alcohols or activated alcohols like mesylates or tosylates or into the bromides or iodides, or finally further elaborated via $S_N2$-reaction with NaCN to give, via nitrils 5a (step c), exhaustive hydrolysis (step d) and reduction (step e), e.g. with borane in tetrahydrofuran, the building blocks (7a). Finally, the alcohols (7a) can be converted into compounds of formula (3) e.g. by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds of formula (3) as methanesulfonates, chlorides or bromides, respectively.

4-Chloromethyl-2-aryl or 2-heteroaryl-oxazoles (4a) with $R^2$ equal hydrogen are preferably prepared from the corresponding aryl or heteroaryl carboxamides and 1,3-dichloroacetone as described e.g. in Bioorg. Med. Chem. Lett. (2000), 10(17), 2041–2044.

Starting compounds of formula (3), wherein A is oxygen and $A^1$ is nitrogen and n is 3 can be obtained e.g. according to Scheme VI:

Scheme VI

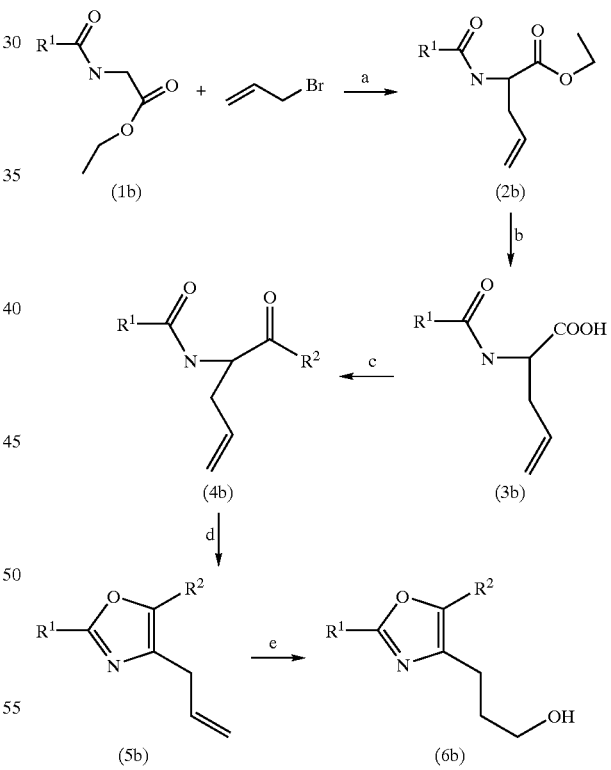

N-Acyl-glycine esters (1b) are either commercially available, known, or can be prepared by standard operations of N-acylation. Mono-allylated esters (2b) can easily be obtained by double deprotonation of (1b) with a strong, non-nucleophilic base like LiHMDS in an aprotic solvent like THF, typically at −78° C., followed by treatment with allyl bromide to produce selectively the C-alkylated products (2b) (step a). Standard hydrolysis generates intermediate acids (3b) (step b), which are then transformed, following well established literature precedence (J. Med. Chem. (1996), 39, 3897), into compounds (4b) (step c). Ring-closure to the oxazole using trifluoro-acetic acid and trifluoro-acetic anhydride as reagents generates key intermediates (5b) (step d), which, finally, are elaborated via hydroboration to the target alcohols (6b), e.g. with 9-BBN in THF and ensuing oxidative work-up with $H_2O_2$ and NaOH (step e). Finally, the alcohols (6b) can be converted into compounds of formula (3) e.g by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds of formula (3) as methanesulfonates, chlorides or bromides, respectively.

Starting compounds of formula (3), wherein A is sulfur and $A^1$ is nitrogen and n is 1 can be obtained e.g. according to Scheme VII:

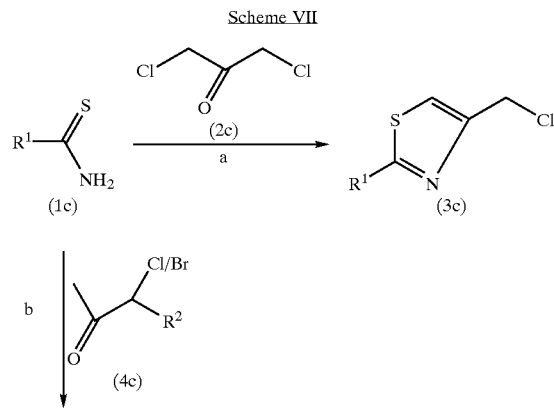

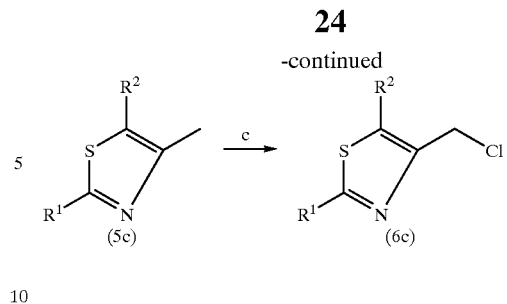

Thioamides (1c) are known or can be prepared by methods known in the art, e.g. by treatment of the corresponding carboxamide with phosphorus pentasulfide or with Lawesson's Reagent [2,4-bis(4-methoxyphenyl)-1,3-dithia-2,4-diphosphetane-2,4-disulfide] in a solvent like toluene at temperatures preferably between 60° C. and the reflux temperature of the solvent. Thioamides (1c) may be condensed with 1,3-dichloroacetone in solvents like acetone or acetonitrile between room temperature and the reflux temperature of the solvents, followed by treatment with strong acid, e.g. concentrated sulfuric acid, preferably at ambient temperature, thus giving chloromethyl compounds (3c) (step a). Alternatively, thioamides (1c) are condensed with alpha-bromo or alpha-chloro ketones (4c) in a solvent like ethanol, preferably at reflux temperature, to give aryl-thiazoles (5c) bearing a methyl function at position 4 (step b) [EP 207453 A2]. By treatment of these aryl-thiazoles (5c) with N-chlorosuccinimide in solvents like acetonitrile, preferably at reflux temperature, chloromethyl compounds (6c) are obtained (step c) [compare WO 0119805 A1].

Starting compounds of formula (3), wherein A is sulfur and $A^1$ is nitrogen and n is 2 or 3 can be obtained e.g. according to Scheme VIII:

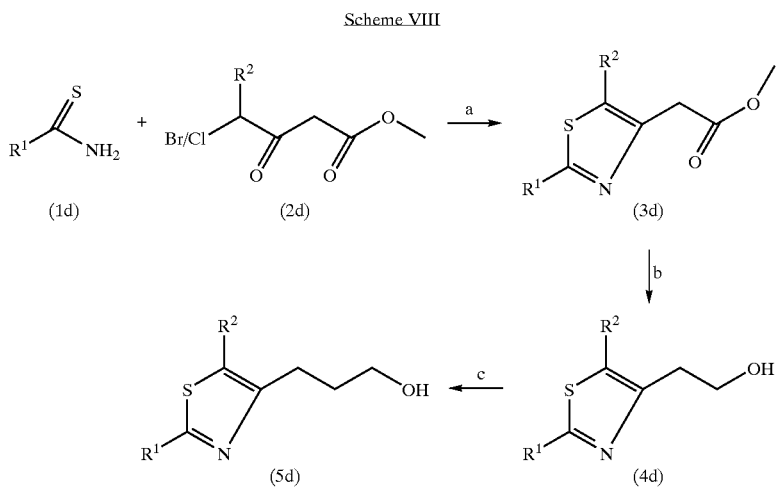

Condensation of thioamides (1d) with a suitable bis-electrophile, e.g. methyl 4-bromo- or 4-chloro-3-oxo-alkanoates (2d), preferably in a solvent like toluene at elevated temperatures (e.g. at reflux temperature), gives thiazoles (3d) carrying an acetic acid ester function at position 4 (step a) [compare WO97/31907 A1]. 4-Bromo-3-oxo-alkanoates (2d) are known or can be prepared by methods known in the art [compare WO 01/79202 A1]. Thiazoles (3d) can then be reduced, e.g. with lithium aluminum hydride, to thiazoles (4d) (step b). Optionally, an elongation of the side chain can then be performed by standard methods, such as transformation of the alcohol function into a leaving group, e.g. a mesylate, ensuing treatment with cyanide, saponification and reduction, affording thiazoles (5d) with a hydroxy-propyl function attached to position 4 (step c). Finally, the alcohols (4d) and (5d) can be activated to the mesylates or tosylates using well known standard procedures.

Starting compounds of formula (3), wherein $A^1$ is sulfur and A is nitrogen and n is 1 can be obtained e.g. according to Scheme IX.

Scheme IX

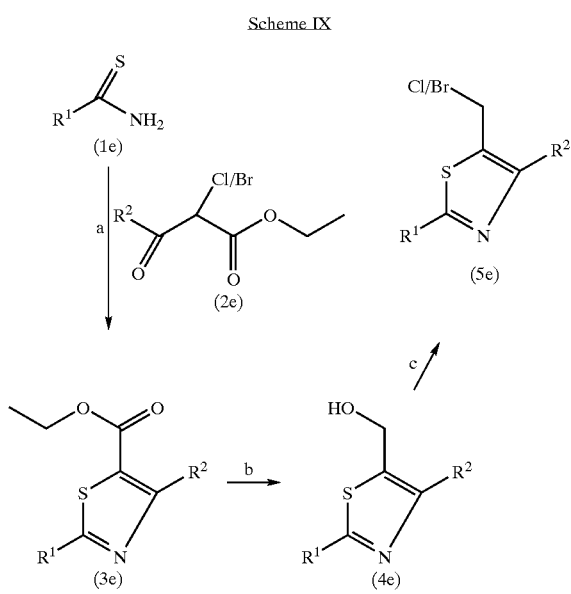

Thioamides (1e) are known or can be prepared by methods known in the art, e.g. by treatment of the corresponding carboxamide with phosphorus pentasulfide or with Lawesson's Reagent [2,4-bis(4-methoxyphenyl)-1,3-dithia-2,4-diphosphetane-2,4-disulfide] in a solvent like toluene at temperatures preferably between 60° C. and the reflux temperature of the solvent. Thioamides (1e) can be reacted with alkyl 2-halo acetoacetates (2e) in solvents like ethanol, preferably at reflux temperature, to give thiazole-carboxylic esters (3e) (step a). Reduction of these esters (3e), preferably using lithium aluminium hydride in a solvent like ether or tetrahydrofuran, preferably between 0° C. and room temperature, gives primary alohols (4e) (step b), which can be used as such or can be converted into the corresponding halides (5e), e.g. by treatment with methanesulfonyl chloride in dichloromethane in the presence of 2,6-lutidine, preferably between −20° C. and the reflux temperature of dichloromethane [compare WO 02/28433], by treatment with thionyl chloride in a solvent like dichloromethane or chloroform preferably at temperatures between −20° C. and +50° C. or by treatment with tetrabromomethane, triphenylphosphine in solvents like tetrahydrofuran at temperatures between 0° C. and the reflux temperature of the tetrahydrofuran (step c).

Starting compounds of formula (3), wherein $A^1$ is oxygen and A is nitrogen and n is 1 can be obtained e.g. according to Scheme X.

Scheme X

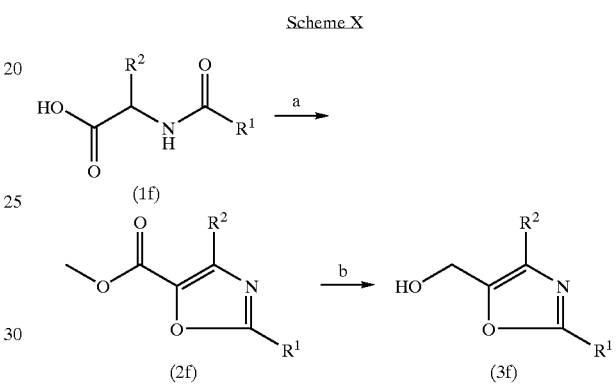

4-Substituted 2-aryloxazol-5-carboxylates (2f) ($R^2$ equal an alkyl or a cycloalkyl group) can be obtained from N-aroyl-amino acids (1f) as described in [J. Chem. Soc., Chem. Commun., 1995, 2335–2336]: i) the N-aroyl-amino acids (1f) are treated with oxalyl chloride in solvents like benzene, dichloromethane or tetrahydrofuran preferably at room temperature followed by evaporation with addition of toluene; ii) the thus obtained crude intermediates are treated with triethylamine and an alcohol preferably between 0° C. and room temperature (step a). Reduction of the ester function in compounds (2f) by well known methods e.g. with diisobutyl aluminium hydride in a solvent like tetrahydrofuran gives primary alcohols (3f) (step b). Finally, the alcohols (3f) can be converted into compounds of formula (3) e.g by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds of formula (3) as methanesulfonates, chlorides or bromides, respectively.

Starting compounds of formula (3), wherein n is 2 or 3 can be obtained from starting compounds of formula (3), wherein n is 1 or 2, e.g. according to Scheme XI.

Scheme XI

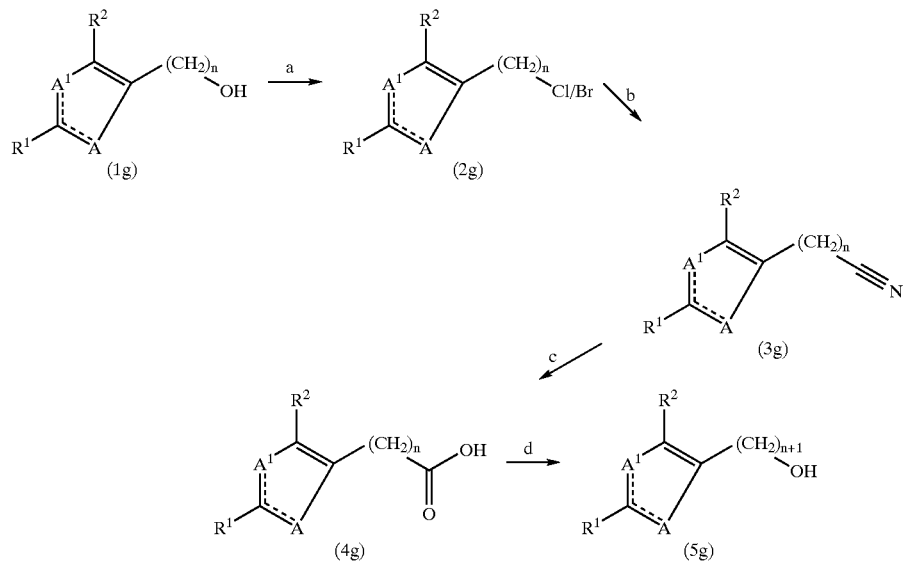

Aryl-oxazole alkanols or aryl-thiazole alkanols (1g) with a chain length of n carbon atoms can be converted into analogues with a chain length of n+1 carbon atoms by methods well known in the art (Scheme XI), e.g. by conversion of the primary alcohol function into a suitable leaving group, e.g. a halide (step a), reaction with cyanide ion (step b), saponification (step c) followed by reduction of the acid formed (compounds (4g)) to the primary alcohols (5g), e.g. by using diborane in tetrahydrofuran (step d). Finally, the alcohols (5g) can be converted into compounds of formula (3) e.g by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds of formula (3) as methanesulfonates, chlorides or bromides, respectively.

Starting compounds of formula (8) can be obtained e. according to Scheme XII or Scheme XIII:

The preparation of 2-carboxy halo indoles (8), wherein $R^6$ represents hydrogen, alkyl or cycloalkyl, by Fischer Indole synthesis reactions is depicted in Scheme XII; the scheme describes the synthesis of 5-halo indoles, but is equally applicable to that of 6-halo indoles, wherein $R^5$ represents hydrogen, alkyl or cycloalkyl:

Scheme XII (part a)

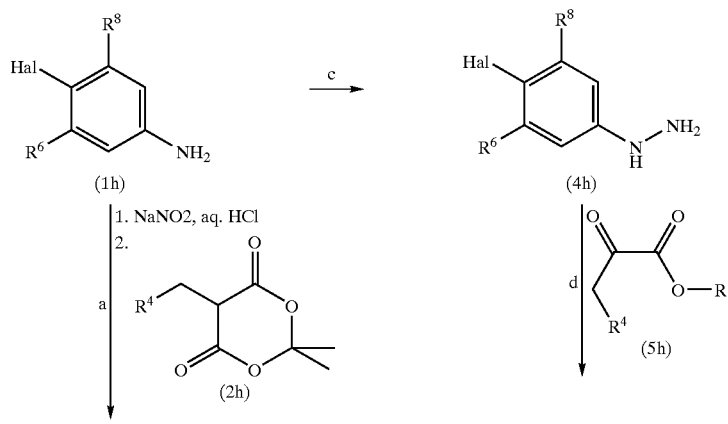

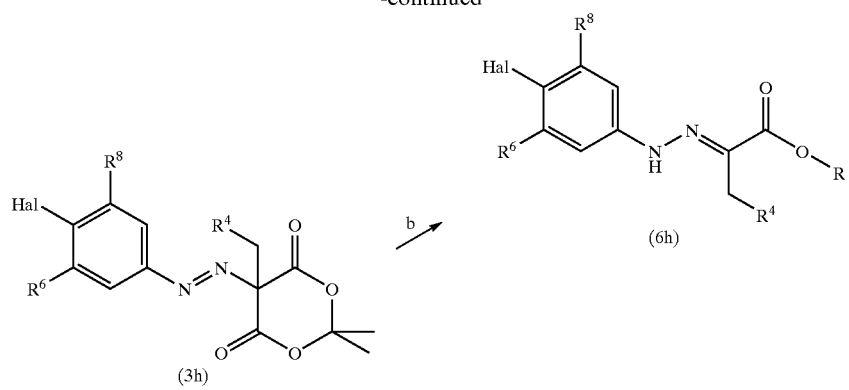

R means alkyl;

Scheme XII (part b)

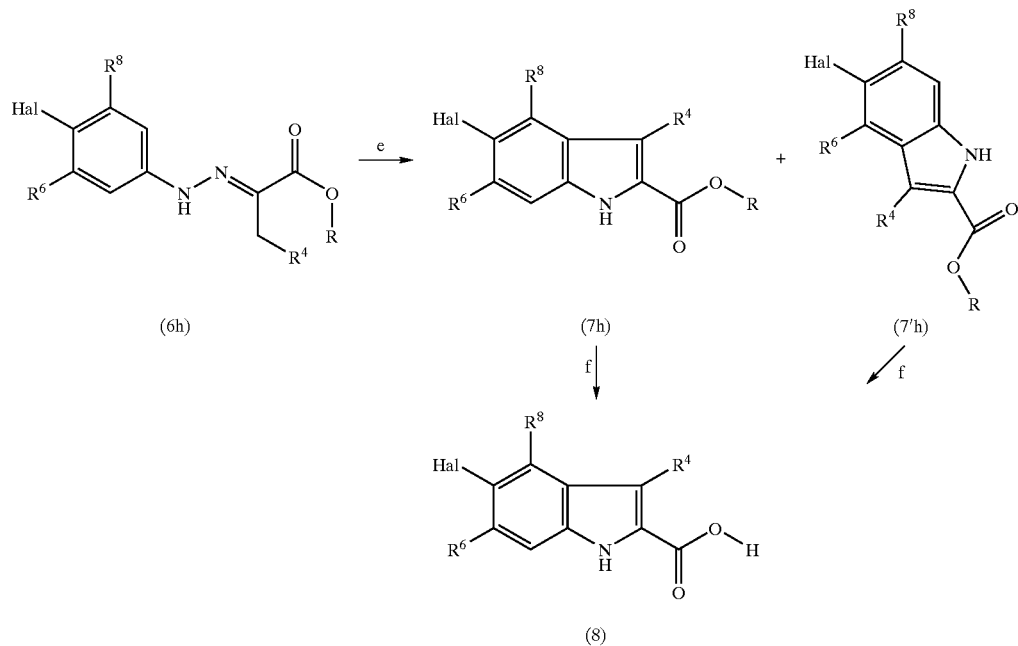

R means alkyl;

Halo-anilines (1h) can be converted in to diazo Meldrum's acids (3h) by diazotization of halo-anilines (1h) with e.g. sodium nitrite in aqueous acid at temperatures around 0° C. followed by reaction with a Meldrum's acid (2h) in solvent mixtures like ethanol/water preferably at close to neutral pH and in a temperature range between 0° C. and 60° C. (compare Organic Process Research & Development (1998), 2, 214–220) (step a). Treatment of compounds (31i) with an alcoholate, preferably sodium ethylate, in the corresponding alkohol, preferably at room temperature gives hydrazones (6h) (compare Organic Process Research & Development (1998), 2, 214–220) (step b). Alternatively, halo-anilines (1h) can be converted into hydrazines (4h) e.g. by treatment with sodium nitrite in hydrochloric acid preferably at temperatures between −10° C. and room temperature followed by subsequent reduction of the diazonium salt formed with e.g. thin(II)-chloride preferably in a similar temperature range (step c). Hydrazines (4h) can then be treated with pyruvic acid derivatives (5h) in a solvent like dichloromethane or toluene preferably at a temperature range between room temperature and the reflux temperature of the solvents optionally with removal of the water formed with molecular sieves or by the use of a Dean Stark trap giving hydrazones (6h) (step d). The indol formation can then be performed by treatment of hydrazones (6h) with e.g. a strong acid like aqueous sulfuric acid or with p-toluenesulfonic acid in a solvent toluene or xylene preferably at elevated temperature up to the reflux temperature of the solvent or with poly-phosphoric acid as reagent and solvent preferably at temperatures between 150° C. and 200° C. (compare J. Chem. Soc. 1955, 3499–3503) (step e). Starting from unsymmetrical halo-anilines (1h), indol isomers 7h and 7'h are formed. The two isomers can be separated by methods known in the art, e.g. by chromatography or crystallization. Isomer 7h and isomer 7'h can serve as intermediates for the preparation of the desired 2-carboxy halo indoles (8), which are obtained by saponification of indole esters (7h or 7'h) e.g. with lithium hydroxide in a mixture of dioxane and water in a temperature range between room temperature and 80° C. (step f).

The preparation of 2-carboxy halo indoles (8), wherein $R^6$ represents hydrogen, alkyl or cycloalkyl, starting from ortho nitro benzaldehyde derivatives is depicted in Scheme XIII; the scheme describes the synthesis of 5-halo indoles, but is equally applicable to that of 6-halo indoles, wherein $R^5$ represents hydrogen, alkyl or cycloalkyl:

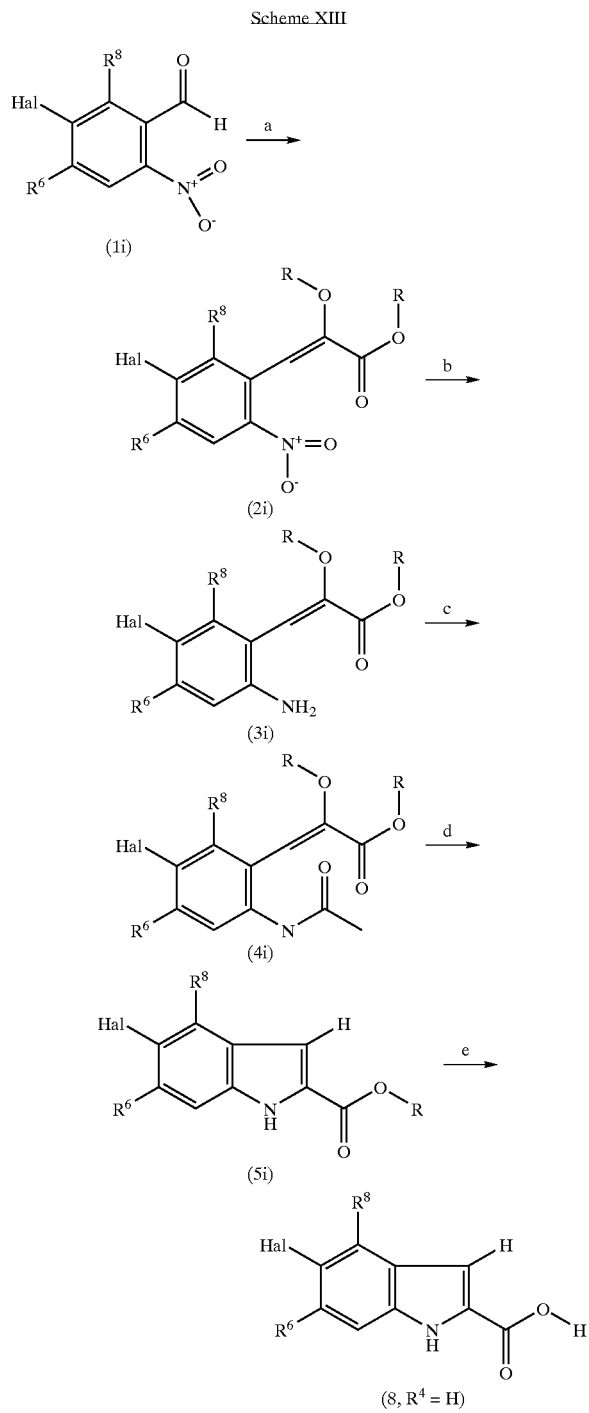

R means alkyl;

Ortho nitro benzaldehyde derivatives (ii) react with a Wittig salt such as such as (1,2-diethoxy-2-oxoethyl)-triphenyl-phosphonium chloride in solvents like isopropanol, dichloromethane or tetrahydrofuran or mixtures thereof in the presence of a base like potassium carbonate or tetramethyl guanidine, preferably between 0° C. and the reflux temperature of the solvents, giving nitrophenyl acrylic esters (2i) as E and/or Z isomers (step a). Reduction of nitro-phenyl acrylic esters (2i) e.g. with iron powder in a solvent like acetic acid preferably between 60° C. and 100° C. gives amino-phenyl acrylic esters (3i) (step b). Acetylation of amino-phenyl acrylic esters (3i) under standard conditions (e.g. acetyl chloride, triethylamine in dichloromethane between 0° C. and room temperature) (step c), gives compounds (4i), which undergo indol formation upon treatment with a strong acid such as p-toluenesulfonic acid in a solvent like toluene preferably at the reflux temperature of the solvent (step d). Saponification of indole esters (5i) e.g. with lithium hydroxide in a mixture of dioxane and water in a temperature range between room temperature and 80° C. gives then 2-carboxy halo indoles (8, $R^4$=H) (step e).

The conversion of a compound of formula I into a pharmaceutically acceptable salt can be carried out by treatment of such a compound with an inorganic acid, for example a hydrohalic acid, such as, for example, hydrochloric acid or hydrobromic acid, sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The corresponding carboxylate salts can also be prepared from the compounds of formula I by treatment with physiologically compatible bases such as sodium or potassium hydroxide or a tertiary amine as triethylamine.

The conversion of compounds of formula I into pharmaceutically acceptable esters or amides can be carried out e.g. by treatment of suited amino or hydroxyl groups present in the molecules with an carboxylic acid such as acetic acid, with a condensating reagent such as benzotriazol-1-yloxytris(dimethylamino)phosphonium hexafluorophosphate (BOP) or N,N-dicylohexylcarbodiimide (DCCI) to produce the carboxylic ester or carboxylic amide.

Preferably, the conversion of compounds of formula I into pharmaceutically acceptable esters can e.g. be carried out by treatment of compounds of formula (I) in the presence of a condensating reagent such as benzotriazol-1-yloxytris(dimethylamino)phosphonium hexafluorophosphate (BOP) or N,N-dicylohexylcarbodiimide (DCCI) and 4-dimethylamino-pyridine with the corresponding alcohol in solvents such as e.g. N,N-dimethylformamide according to methods well known in the art.

Preferred is a process for the preparation of a compound according to formula I comprising one of the following reactions:

reaction of a compound according to formula

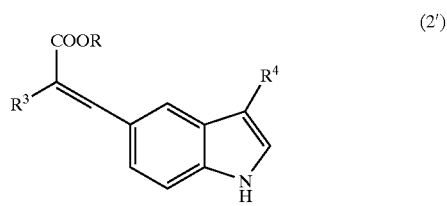

in the presence of a compound according to formula

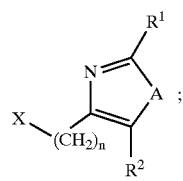
(3')

reaction of a compound according to formula

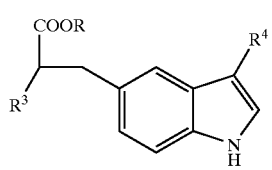
(4')

in the presence of a compound according to formula

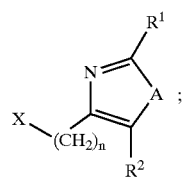
(3')

hydrogenation of a compound according to formula

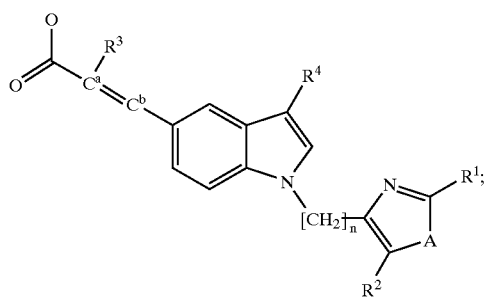
(Ia)

wherein
$R^3$ is alkoxy or alkoxy substituted with one to three halogen atoms; $R^5$ is

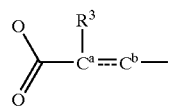

wherein the bond between the carbon atoms $C^a$ and $C^b$ is a carbon carbon single or double bond; $R^6$ is hydrogen; $R^7$ is hydrogen; $R^8$ is hydrogen; A is oxygen or sulfur; $A^1$ is nitrogen; X is halogen or $CH_3SO_3$ and R is alkyl, aryl or aralkyl.

Further preferred is a process for the preparation of a compound according to formula I comprising one of the following reactions:

reaction of a compound according to formula

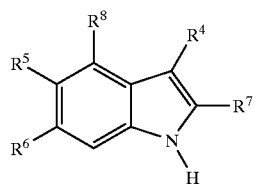
(2")

in the presence of a compound according to formula

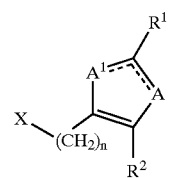
(3)

wherein any one of $R^5$ and $R^6$ is

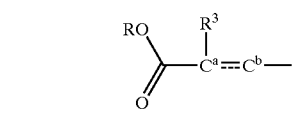

and the other is hydrogen, alkyl or cycloalkyl and, wherein the bond between the carbon atoms $C^a$ and $C^b$ is a carbon carbon single or double bond; X is halogen or $CH_3SO_3$; R is alkyl, aryl or aralkyl; $R^1$ to $R^4$, $R^7$, $R^8$, A, $A^1$ and n are defined as before. Preferred is the above reaction in a solvent such as N,N-dimethylformamide or N-methly-pyrrolidone in the presence of a base such as e.g. sodium hydride or potassium tert-butylate, preferable between 0° C. and room temperature followed by hydrolysis of the ester function, preferably with LiOH or NaOH in solvent mixtures like dioxane/water, tetrahydrofuran or ethanol/water preferable between 0° C. and room temperature. Further preferred is the above reaction in the presence of KOH in DMSO between 0° C. and 80° C. preferably at 22° C.

hydrogenation of a compound according to formula

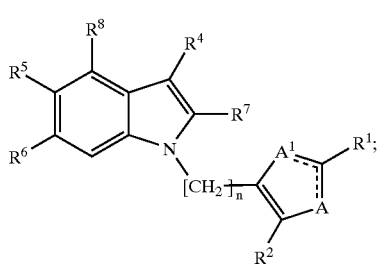
(Ik)

wherein any one of $R^5$ and $R^6$ is

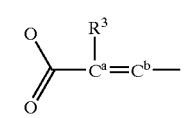

and the other is hydrogen, alkyl or cycloalkyl; and wherein the bond between the carbon atoms $C^a$ and $C^b$ is a carbon carbon double bond; $R^1$ to $R^4$, $R^7$, $R^8$, A, $A^1$ and n are defined as before. Preferred is the above hydrogenation in the presence of palladium on charcoal in solvents like methanol, ethanol, dichloromethane or tetrahydrofuran or mixtures thereof.

Preferred intermediates are:

(Z)-2-Ethoxy-3-(1H-indol-5-yl)-acrylic acid ethyl ester; rac-2-Ethoxy-3-(1H-indol-5-yl)-propionic acid ethyl ester;
(S)-2-Ethoxy-3-(1H-indol-5-yl)-propionic acid;
(S)-2-Ethoxy-3-(1H-indol-5-yl)-propionic acid methyl ester;
(R)-2-Ethoxy-3-(1H-indol-5-yl)-propionic acid ethyl ester;
(Z)-3-(1H-Indol-5-yl)-2-methoxy-acrylic acid benzyl ester;
rac-2-Ethoxy-3-(3-methyl-1H-indol-5-yl)-propionic acid ethyl ester;
rac-2-Ethoxy-3-(2-methyl-1H-indol-5-yl)-propionic acid ethyl ester;
rac-3-(1H-Indol-5-yl)-2-propoxy-propionic acid methyl ester;
rac-3-(1H-Indol-5-yl)-2-phenoxy-propionic acid methyl ester;
rac-3-(1H-Indol-5-yl)-2-isopropoxy-propionic acid methyl ester;
rac-2-But-3-enyloxy-3-(1H-indol-5-yl)-propionic acid methyl ester;
rac-2-Ethoxy-3-(4-methyl-1H-indol-5-yl)-propionic acid ethyl ester and
rac-2-Ethoxy-3-(1H-indol-6-yl)-propionic acid ethyl ester.

As described above, the compounds of formula (I) of the present invention can be used as medicaments for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases (such as e.g. crown disease, inflammatory bowel disease, collitis, pancreatitis, cholestasis/fibrosis of the liver, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment and/or prevention of non-insulin dependent diabetes mellitus is preferred.

The compounds of formula I described above for use as therapeutically active substances are a further object of the invention. Preferred is the use as therapeutically active substances for the prophylaxis and/or therapy of diabetes, non-insulin dependent diabetes mellitus, elevated blood pressure, increased lipid and cholesterol levels, atherosclerotic diseases or metabolic syndrome and particularly preferred non-insulin dependent diabetes mellitus.

Also an object of the invention are compounds described above for the preparation of medicaments for the prophylaxis and/or therapy of diseases which are modulated by PPARα and/or PPARγ agonists, preferably for the production of medicaments for the prophylaxis and/or therapy of diabetes, non-insulin dependent diabetes mellitus, elevated blood pressure, increased lipid and cholesterol levels, atherosclerotic diseases or metabolic syndrome and particularly preferred non-insulin dependent diabetes mellitus.

Likewise an object of the invention are pharmaceutical compositions comprising a compound of formula I described above and a therapeutically inert carrier. Another object of the present invention is the above pharmaceutical composition further comprising a therapeutically effective amount of a lipase inhibitor particularly, wherein the lipase inhibitor is orlistat.

An object of the invention is also the use of the compounds described above for the production of medicaments, particularly for the treatment and/or prophylaxis of diseases which are modulated by PPARα and/or PPARγ agonists, preferably diabetes, non-insulin dependent diabetes mellitus, elevated blood pressure, increased lipid and cholesterol levels, atherosclerotic diseases or metabolic syndrome and particularly preferred non-insulin dependent diabetes mellitus.

A further object of the present invention is the use of a compound of formula I in the manufacture of a medicament for the treatment and/or prophylaxis of diseases which are modulated by PPARα and/or PPARγ agonists in a patient who is also receiving treatment with a lipase inhibitor. Preferred is the above use, wherein the lipase inhibitor is orlistat. Particularly preferred is the above use for the treatment and/or prophylaxis of diseases, wherein the diseases are diabetes, non-insulin dependent diabetes mellitus, elevated blood pressure, increased lipid and cholesterol levels, atherosclerotic diseases or metabolic syndrome and particularly preferred non-insulin dependent diabetes mellitus.

A further object of the invention comprises compounds which are manufactured according to one of the described processes.

A further object of the invention is a method for the treatment and/or prophylaxis of diseases which are modulated by PPARα and/or PPARγ agonists, preferably diabetes, non-insulin dependent diabetes mellitus, elevated blood pressure, increased lipid and cholesterol levels, atherosclerotic diseases or metabolic syndrome and particularly preferred non-insulin dependent diabetes mellitus, whereby an effective amount of a compound of formula I is administered. Another object of the present invention is the above method which further comprises administration to the human a therapeutically effective amount of a lipase inhibitor, particularly, wherein the lipase inhibitor is orlistat. The above method for simultaneous, separate or sequential administration is also an object of the present invention.

Assay Procedures

The following tests can be used in order to determine the activity of the compounds of formula I.

Background information on the performed assays can be found in: Nichols J S et al. "Development of a scintillation proximity assay for peroxisome proliferator-activated receptor gamma ligand binding domain", (1998) Anal. Biochem. 257: 112–119.

Full-length cDNA clones for human PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in E. coli strain BL21

(pLysS) cells by standard methods (Ref: Current Protocols in Molecular Biology, Wiley Press, edited by Ausubel et al.).
Radioligand Binding Assay PPARα receptor binding was assayed in TKE10 (10 mM Tris-HCl, pH 8, 50 mM KCl, 2 mM EDTA, 0.1 mg/n fatty acid free BSA and 10 mM DTT). For each 96 well 2.4 ug equivalent of GST-PPARα-LBD fusion protein and radioligand, e.g. 40000 dpm 2(S)-(2-benzoyl-phenylamino)-3-{4-[1,1-ditritio-2-(5-methyl-2-phenyl-oxazol-4-yl)-ethoxy]-phenyl}-propionic acid, were incubated in 100 ul volume at RT for 2 hrs. Bound ligand was removed from unbound ligand by solid phase separation using MultiScreen plates (Millipore) filled with 80 ul of SG25 according to the manufacturer's recommendations.

PPARγ receptor binding was assayed in TKE50 (50 mM Tris-HCl, pH 8, 50 mM KCl, 2 nM EDTA, 0.1 mg/ml fatty acid-free 13SA and 10 mM DTT). For each 96 well reaction an 140 ng equivalent of GST-PPARγ-LBD fusion protein was bound to 10 ug SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the recptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 ul were added, the reaction incubated at RT for 1h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6 well plates at a density of $10^5$ Cells/well and then transiently batch-transfected with either the pFA-PPARγ-LBD or pFA-PPARα-LBD expression plasmids plus the pFR-luc reporter plasmid and an expression plasmid encoding the secretable form of alkaline phosphatase (SEAP) as a normalization control. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final. 0.1% DMSO). Following incubation of the cells for 24 hours with substances, 50 ul of the supernatant was recovered and analyzed for SEAP activity (Roche Molecular Biochemicals). The remainder of the supernatant was discarded, 50 ul PBS was added per well followed by one volume of Luciferase Constant-Light Reagent (Roche Molecular Biochemicals) to lyse the cells and initiate the luciferase reaction. Luminescence for both SEAP and luciferase was measured in a Packard TopCount. Luciferase activity was normalized to the SEAP control and transcriptional activation in the presence of a test substance was expressed as fold-activation over cells incubated in the absence of the substance. EC50 values were calculated using the XLfit program (ID Business Solutions Ltd. UK).

The compounds of the present invention exhibit $IC_{50}$ values of 0.1 nM to 50 μM, preferably 1 nM to 10 μM, particularly—1–3500 nM, more preferred 20 to 1000 nM, for PPARα and PPARγ. The compounds further exhibit $EC_{50}$ values of 0.1 nM to 50 μM, preferably 1 nM to 10 μM, more preferably—1–3500 nM, particularly 20 to 1000 nM, for PPARα and PPARγ.

The following table shows measured values for some selected compounds of the present invention and for a compound already known in the art (e.g.: Rosiglitazone, Drugs 1999, Vol 57(6), 921–930).

|  | PPARα $IC_{50}$ (μM) | PPARγ $IC_{50}$ (μM) | PPARα $EC_{50}$ (μM) | PPARγ $EC_{50}$ (μM) |
|---|---|---|---|---|
| Example 5 | 0.24 | 0.36 | 1.52 | 0.17 |
| Example 8 | 0.28 | 0.40 | 0.19 | 0.56 |
| Example 18 | 0.03 | 0.18 | 0.08 | 0.13 |
| Example 21 | 0.03 | 0.005 | 0.03 | 0.07 |
| Example 25 | 0.12 | 0.05 | 0.06 | 0.05 |
| Example 39 | 0.06 | 0.11 | 0.47 | 0.02 |
| Example 44 | 1.64 | 1.41 | 5.24 | 2.70 |
| Rosiglitazone | inactive | 1.1 | inactive | 0.41 |

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, vetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 0.1 mg to about 1000 mg, especially about 0.1 mg to about 100 mg, comes into consideration. Further preferred daily dosages for adult patients are of about 1 mg to about 1000 mg, especially about 1 mg to about 100 mg. Depending on the dosage it is convenient to administer the daily dosage in several dosage units.

The pharmaceutical preparations conveniently contain about 0.05–500 mg, preferably 0.05–100 mg, of a compound of formula I. Preferred pharmaceutical preparations comprise about 0.5–500 mg, preferably 0.5–100 mg, of a compound of formula I.

The following Examples serve to illustrate the present invention in more detail. They are, however, not intended to limit its scope in any manner.

EXAMPLES a) Preparation of Intermediates:

Preparation 1

Rac-2-Ethoxy-3-(1H-indol-5-yl)-propionic Acid Ethyl Ester (Z)-2-Ethoxy-3-(1H-indol-5-yl)-acrylic Acid Ethyl Ester To a solution of 25.73 g of (1,2-diethoxy-2-oxoethyl) triphenyl phosphonium chloride in 200 ml of dichloromethane was added at 0° C. 8.0 ml of tetramethyl guanidine and the mixture was warmed to 22° C. The mixture was treated with 5.81 g of 5-formyl-indole and stirring was continued at 40° C. for 16 h. The mixture was treated again with 25.73 g of the Wittig salt and 8.0 ml of tetramethyl guanidine and stirring was continued at 40° C. for 24 h after which time the conversion was complete. The mixture was evaporated and the residue partitioned between AcOEt and water. The organic layer was dried, evaporated and the residue chromatographed on silica (n-hexane/AcOEt, 2:1) to give 9.80 g of the title compound as an oil which solidified on storing at 22° C. to give a pale yellow solid. MS: (M)+ 259.2.

Rac-2-Ethoxy-3-(1H-indol-5-yl)-Propionic Acid Ethyl Ester

A suspension of 9.7 g of (Z)-2-ethoxy-3-(1H-indol-5-yl)-acrylic acid ethyl ester in 100 ml of EtOH and 1.0 g of Pd/C (10%) was hydrogenated at 22° C. for 2 h after which time hydrogen uptake ceased. The suspension was filtered, the filtrate evaporated and the residue chromatographed on silica (n-hexane/AcOEt, 2:1) to give 8.7 g of the title compound as a white solid. MS: (M)+ 261.2.

Preparation 2

(R)-2-Ethoxy-3-(1H-indol-5-yl)-propionic Acid Ethyl Ester and (S)-2-ethoxy-3-(1H-indol-5-yl)-propionic Acid Methyl Ester A solution of 5.00 g of rac-2-ethoxy-3-(1H-indol-5-yl)-propionic acid ethyl ester in 170 ml of t-butyl methyl ether was emulsified with 675 ml of 0.1 M sodium chloride, 3 mM sodium phosphate pH 7.0 by vigorous stirring. 200 mg of Chirazyme L-6 (commercially available from Roche Diagnostics) was added and the pH maintained at 7.0 by the controlled addition of 0.1 N sodium hydroxide solution (pH-stat) under vigorous stirring. After a consumption of 81.6 ml (43% conversion; 5.7 h) the reaction mixture was extracted (2×500 ml dichloromethane) to give the (R)-enriched ethyl ester. The aqueous phase was acidified to pH 2.5 and extracted (3×500 ml dichloromethane) to give 1.64 g of (S)-2-ethoxy-3-(1H-indol-5-yl)-propionic acid as a yellowish foam, ee=94% (Chiralcel-OJ, 25 cm×4.6 mm; 80% heptane/20% (EtOH+1.5% TFA). MS: (M)+ 233.1. $[\alpha]_D$=−30.0° (1.1% in EtOH).

A stirred solution of 0.70 g of the (S)-acid in 6 ml of methanol and 0.6 ml of water was treated with a 0.6 M solution of diazomethane in ethylether until gas evolution ceased (15 ml). The mixture was evaporated and the residue chromatographed on RP-18 ($CH_3CN/H_2O$, 1:1) to give 0.37 g of (S)-2-ethoxy-3-(1H-indol-5-yl)-propionic acid methyl ester as a brown oil. MS: (M+H)+ 248.2.

The (R)-enriched ester (2.91 g, 81% ee) was subjected to a second, analogous enzymatic hydrolysis (100 ml t-butyl methyl ether, 400 ml buffer, 30 mg Chirazyme L-6). After a consumption of 12.4 ml of titrating agent (45 h) the reaction mixture was extracted (3×500 ml dichloromethane) to give 2.45 g of (R)-2-ethoxy-3-(1H-indol-5-yl)-propionic acid ethyl ester as a brown oil, ee=96% (conditions see above). MS: (M+H)+ 262.1, (M+$NH_4$)+ 279.1. $[\alpha]_D$=+10.5° (1.1% in EtOH).

Preparation 3

(Z)-3-(1H-indol-5-yl)-2-methoxy-acrylic Acid Benzyl Ester

To a solution of 3.70 g of (1-methoxy-2-benzyloxy-oxoethyl)triphenyl phosphonium chloride in 60 ml of dichloromethane was added at 0° C. 1.07 ml of tetramethyl guanidine and the mixture was warmed to 22° C. The mixture was treated with 2.25 g of 5-formyl-indole and stirring was continued at 40° C. for 16 h. The mixture was treated again with 3.70 g of the Wittig salt and 1.07 ml of tetramethyl guanidine and stirring was continued at 40° for 24 h after which time the conversion was complete. The mixture was evaporated and the residue partitioned between AcOEt and water. The organic layer was dried, evaporated and the residue chromatographed on silica (n-hexane/AcOEt, 4:1) to give 1.67 g of the title compound as a pale yellow oil. MS: (M+H)+ 308.2.

Preparation 4

Rac-2-Ethoxy-3-(3-methyl-1H-indol-5-yl)-propionic Acid Ethyl Ester

In analogy to the procedures described in preparation 1a) and 1b), 3-methyl-1H-indole-5-carbaldehyde [Helv. Chim. Acta (1968), 51(7), 1616–28] was reacted with (1,2-diethoxy-2-oxoethyl)triphenyl phosphonium chloride in dichloromethane in the presence of tetramethyl guanidine to give.(Z)-2-ethoxy-3-(3-methyl-1H-indol-5-yl)-acrylic acid ethyl ester, which was subsequently hydrogenated to yield the title compound as colorless oil.

MS: (M+H)+ 276.3.

Preparation 5

Rac-2-Ethoxy-3-(2-methyl-1H-indol-5-yl)-propionic Acid Ethyl Ester

2-Methyl-1H-indole-5-carbaldehyde

A mixture of 3.9 g 2-methyl-1H-indole-5-carbonitrile [Journal of Organic Chemistry (1994), 9(21), 6372–7], 7.22 g sodium hypophosphite monohydrate and 2.60 g Raney-Nickel in 110 ml acetic acid (50%)/pyridine 1:1 was stirred at 45° C. for 75 min. After cooling down to room temperature, the reaction mixture was filtered (dicalite), then the filtrate poured into ice-water and extracted 3 times with EtOAc. The combined organic phases were washed with water, dried over magnesium sulfate and evaporated. The residue was crystallized from n-heptane to give 3.19 g of 2-methyl-1H-indole-5-carbaldehyde as light red solid.

MS: (M)+ 159.1.

ac-2-Ethoxy-3-(2-methyl-1H-indol-5-yl)-propionic acid ethyl ester

In analogy to the procedures described in preparation 1a) and 1b), 2-methyl-1H-indole-5-carbaldehyde was reacted with (1,2-diethoxy-2-oxoethyl)triphenyl phosphonium chloride in dichloromethane in the presence of tetramethyl guanidine to give (Z)-2-ethoxy-3-(2-methyl-1H-indol-5-yl)-acrylic acid ethyl ester, which was subsequently hydrogenated to yield the title compound as colorless oil.

MS: $(M+H)^+$ 276.3.

Preparation 6

Rac-3-(1H-Indol-5-yl)-2-propoxy-propionic Acid Methyl Ester 1-(2-Trimethylsilanyl-ethoxymethyl)-1H-indole-5-carbaldehyde To a stirred suspension of 5.45, sodium hydride (55%) in mineral oil) in 100 ml N,N-dimethylformamide was added at 0–5° C. a solution of 16.8 g indole-5-carboxaldehyde in 100 ml N,N-dimethylformamide followed by 24.46 ml of 2-(trimethylsilyl)-ethoxymethyl chloride. The reaction mixture was then warmed up to ambient temperature and stirring continued for 16 hours. It was then poured onto ice, neutralized to pH 4 with HCl (1N) and extracted 3 times with ethyl acetate. The combined organic phases were washed with water, dried over magnesium sulfate and evaporated to give a brown oil, which was purified by chromatography (silicagel, eluent: gradient of n-heptane/EtOAc) to yield 25.52 g 1-(2-trimethylsilanyl-ethoxymethyl)-1H-indole-5-carbaldehyde as light yellow oil.

MS: $(M)^+$ 275.2.

3-Hydroxy-2-propoxy-3-[1-(2-trimethylsilanyl-ethoxymethyl)-1H-indol-5-yl]-propionic Acid Ethyl Ester (Mixture of Diasteromers)

To a solution of 30 mmol lithium-diisopropylamide in 50 ml tetrahydrofuran were added at −78° C. 4.39 g propoxy-acetic acid ethyl ester [Journal of the American Chemical Society (1996), 118(41), 9901–9907] dissolved in 25 ml of tetrahydrofuran; after 30 min. stirring at −78° C., a solution of 3.31 g 1-(2-trimethylsilanyl-ethoxymethyl)-1H-indole-5-carbaldehyde in 30 ml tetrahydrofuran was added and after another 30 min., the reaction mixture was quenched with 25 ml $H_2O$ and then warmed up to ambient temperature. It was then extracted with ethyl acetate and the combined organic phases were washed with water, dried over magnesium sulfate and evaporated to give a light brown oil which was purified by chromatography (silicagel, eluent: gradient of n-heptane/EtOAc) to yield 4.65 g 3-hydroxy-2-propoxy-3-[1-(2-trimethylsilanyl-ethoxymethyl)-1H-indol-5-yl]-propionic acid ethyl ester (mixture of diasteromers) as a yellow oil.

MS: $(M+NH_4)^+$ 439.4.

2-Propoxy-3-[1-(2-trimethylsilanyl-ethoxymethyl)-1H-indol-5-yl]-(Z,E)-acrylic Acid Ethyl Ester 3.67 g 3-Hydroxy-2-propoxy-3-[1-(2-trimethylsilanyl-ethoxymethyl)-1H-indol-5-yl]-propionic acid ethyl ester (mixture of diasteromers) were dissolved in 100 ml dichloromethane and cooled to 0° C.; then treated with 1.40 ml of triethyl amine followed by 0.67 ml of methanesulfonyl chloride. After two hours stirring at 0° C., the reaction mixture was poured into a cold solution of sodium hydrogencarbonate in water and extracted with ethyl acetate to yield after drying over magnesium sulfate and evaporation 3.65 g of crude 3-chloro-2-propoxy-3-[1-(2-trimethylsilanyl-ethoxymethyl)-1H-indol-5-yl]-propionic acid ethyl ester (mixture of diasteromers). This crude intermediate was dissolved in 100 ml tetrahydrofuran and treated with 3.82 g of 0,1,8-diazabicyclo[5.4.0.1undec-7-ene(1,5,5). The reaction mixture was then stirred for 8 hours at 50° C.; subsequently poured onto ice, neutralized to pH 4 with HCl (1N) and extracted 3 times with ethyl acetate. The combined organic phases were washed with water, dried over magnesium sulfate and evaporated to give a light brown oil which was purified by chromatography (silicagel, eluent: gradient of n-heptane/EtOAc) to yield 1.84 g 2-propoxy-3-[1-(2-trimethylsilanyl-ethoxymethyl)-1H-indol-5-yl]-(Z,E)-acrylic acid ethyl ester as light yellow oil.

MS: $(M+H)^+$ 404.5.

Rac-2-Propoxy-3-[1-(2-trimethylsilanyl-ethoxymethyl)-1H-indol-5-yl]-propionic Acid Ethyl Ester 1.81 g 2-Propoxy-3-[1-(2-trimethylsilanyl-ethoxymethyl)-1H-indol-5-yl]-(Z,E)-acrylic acid ethyl ester were hydrogenated with 0.45 g Pd—C 10% in 75 nm ethanol; after 90 min., the reaction mixture was filtered and evaporated to yield 1.67 g crude product which was purified by chromatography (silicagel, eluent: gradient of n-heptane/EtOAc) to give 1.43 g rac-2-propoxy-3-[1-(2-trimethylsilanyl-ethoxymethyl)-1H-indol-5-yl]-propionic acid ethyl ester as light yellow oil.

MS: $(M+H)^+$ 406.4.

Rac-2-Propoxy-3-[1-(2-trimethylsilanyl-ethoxymethyl)-1H-indol-5-yl]-propionic Acid 1.23 g rac-2-propoxy-3-[1-(2-trimethylsilanyl-ethoxymethyl)-1H-indol-5-yl]-propionic acid ethyl ester were dissolved in 40 ml dioxane, then treated with 7.6 ml lithium hydroxide solution (1 molar in water) and stirred for 16 hours at ambient temperature. Extraction of the reaction mixture with $H_2O$/HCl and dichloromethane, followed by drying of the organic phase with sodium sulfate and evaporation, gave 1.27 g crude product, which was purified by chromatography (silicagel, eluent: gradient of n-heptane/EtOAc) yield to 0.98 g rac-2-propoxy-3-[1-(2-trimethylsilanyl-ethoxymethyl)-1H-indol-5-yl]-propionic acid as a light yellow oil.

MS: $(M-H)^-$ 376.3.

Rac-3-(1H-Indol-5-yl)-2-propoxy-propionic Acid 0.96 g rac-2-propoxy-3-[1-(2-trimethylsilanyl-ethoxymethyl)-1H-indol-5-yl]-propionic acid were dissolved in 40 ml N,N-dimethylformamide. 0.94 ml Ethylene diamine were added, followed by 7.63 ml of a tetrabutylammonium fluoride solution (1 molar in tetrahydrofuran); a small amount of molecular sieves was then added to the reaction mixture and it was heated to 80° C. After 6 hours, the mixture was cooled to r.t., filtered and the filtrate was poured into ice water and extracted 3 times with dichloromethane. The organic phases were washed with water, dried over $MgSO_4$, filtered again and evaporated. The crude rac-3-(1H-indol-5-yl)-2-propoxy-propionic acid was used for the next step without purification.

Rac-3-(1H-Indol-5-yl)-2-propoxy-propionic Acid Methyl Ester

Crude rac-3-(1H-indol-5-yl)-2-propoxy-propionic acid was dissolved in 5 ml N,N-dimethylformamide, 0.54 g of sodium hydrogencarbonate was added followed by 0.32 nm of methyl iodide. The mixture was stirred at r.t. for 7 hours, then poured into ice water and extracted 3 times with ethyl acetate; after drying over $MgSO_4$ and evaporation, the crude product was purified by chromatograph) (silicagel, eluent: gradient of n-heptane/ethyl acetate) to yield 0.47 g of rac-3-(1H-indol-5-yl)-2-propoxy-propionic acid methyl ester as light yellow oil.

MS: $(M)^+$ 261.1

Preparation 7

Rac-3-(1H-Indol-5-yl)-2-phenoxy-propionic Acid Methyl Ester

In anlogy to the procedures described in preparations 6b) to 6g), the title compound has been obtained from 1-(2-trimethylsilanyl-ethoxymethyl)-1H-indole-5-carbaldehyde [preparation 6a)] and phenoxy-acetic acid ethyl ester as colorless oil.

MS: $(M+H)^+$ 296.2.

Preparation 8

Rac-3-(1H-Indol-5-yl)-2-isopropoxy-propionic Acid Methyl Ester

In anlogy to the procedures described in preparations 6b) to 6g), the title compound has been obtained from 1-(2-trimethylsilanyl-ethoxymethyl)-1H-indole-5-carbaldehyde [preparation 6a)] and isopropoxy-acetic acid ethyl ester [Tetrahedron (1982), 38(17), 2733–9] as light yellow solid.

MS: $(M+H)^+$ 262.1.

Preparation 9

Rac-2-But-3-enyloxy-3-(1H-indol-5-yl)-propionic Acid Methyl Ester

1-Benzenesulfonyl-1H-indole-5-carbaldehyde 15.8 g Indole-5-carboxaldehyde were dissolved in 300 ml tetrahydrofuran and cooled to 0° C. Then, 5.12 g sodium hydride (55% in mineral oil) were added in small portions followed by slow, trop by trop addition of 15.2 ml of benzenesulfonyl chloride. The reaction mixture was then warmed up to ambient temperature and stirring continued for 16 hours. It was then poured onto ice, neutralized to pH 4 with HCl (1N) and extracted 3 times with ethyl acetate. The combined organic phases were washed with water, dried over magnesium sulfate and evaporated to give a crude product which was purified by chromatography (silicagel, eluent: gradient of n-heptane/ethyl acetate) to yield 4.09 g 1-benzenesulfonyl-1H-indole-5-carbaldehyde as rose solid.

MS: $(M)^+$ 285.1.

3-(1-Benzenesulfonyl-1H-indol-5-yl)-2-but-3-enyloxy-3-hydroxy-propionic Acid Ethyl Ester (Mixture of Diasteromers)

To a solution of 17.7 ml lithium diisopropylamide (2 molar in tetrahydrofuran) in 40 ml tetrahydrofuran was added a solution of 5.61 g but-3-enyloxy-acetic acid ethyl ester [Tetrahedron (1982), 38(17), 2733–9] in 30 ml tetrahydrofuran at −78° C. After stirring for 30 min., a solution of 4.05 g 1-benzenesulfonyl-1H-indole-5-carbaldehyde in 30 ml tetrahydrofuran was added and stirring at −78° C. continued for additional 30 min. Then, the reaction mixture was quenched with 50 ml of saturated of ammonium chloride solution in water and warmed to ambient temperature. It was then extracted with ethyl acetate and the combined organic phases were washed with water, dried over magnesium sulfate and evaporated to give a crude product which was purified by chromatography (silicagel, eluent: gradient of n-heptane/ethyl acetate) to give 4.37 g of 3-(1-benzenesulfonyl-1H-indol-5-yl)-2-but-3-enyloxy-3-hydroxy-propionic acid ethyl ester (mixture of diasteromers) as colorless oil.

MS: $(M)^+$ 443.2.

3-(1-Benzenesulfonyl-1H-indol-5-yl)-2-but-3-enyloxy-(Z,E)-acrylic Acid Ethyl Ester 3.87 g 3-(1-Benzenesulfonyl-1H-indol-5-yl)-2-but-3-enyloxy-3-hydroxy-propionic acid ethyl ester (mixture of diasteromers) were dissolved in 200 ml benzene and 0.16 g p-toluene sulfonic acid were added; then, the mixture was stirred at 80° C. for 16 hours. After evaporation of the solvent, the residue was purified by chromatography (silicagel, eluent: gradient of n-heptane/dichloromethane) to yield 3.28 g of 3-(1-benzenesulfonyl-1H-indol-5-yl)-2-but-3-enyloxy-(Z,E)-acrylic acid ethyl ester as light yellow oil.

MS: $(M+H)^+$ 426.1.

Rac-2-But-3-enyloxy-3-(1H-indol-5-yl)-propionic Acid Methyl Ester 2.97 g 3-(1-Benzenesulfonyl-1H-indol-5-yl)-2-but-3-enyloxy-(Z,E)-acrylic acid ethyl ester were dissolved in 100 ml methanol. Then, 1.70 g of magnesium(0) were added and the reaction mixture heated to 60° C. After 15 min., it was cooled down to ambient temperature and stirring continued for 4 hours. Then, the solvent was evaporated and the residue was poured onto ice, neutralized to pH 4 with HCl (1N) and extracted 3 times with ethyl acetate. The combined organic phases were washed with water, dried over magnesium sulfate and evaporated to give a crude product which was purified by chromatography (silicagel, eluent: gradient of n-heptane/ethyl acetate) to yield 1.60 g rac-2-but-3-enyloxy-3-(1H-indol-5-yl)-propionic acid methyl ester as light yellow oil.

MS: $(M+H)^+$ 274.2.

Preparation 10

Rac-2-Ethoxy-3-(4-methyl-1H-indol-5-yl)-propionic Acid Ethyl Ester

3-(3-Bromo-2-methyl-6-nitro-phenyl)-2-ethoxy-(Z,E)-acrylic Acid Ethyl Ester

In analogy to the procedure described in preparation 1a), 3-bromo-2-methyl-6-nitro-benzaldehyde [Eur. Pat. Appl. (1982), EP 54180 A2] was reacted with (1,2-diethoxy-2-oxoethyl)triphenyl phosphonium chloride in dichloromethane in the presence of tetramethyl guanidine to yield 3-(3-bromo-2-methyl-6-nitro-phenyl)-2(Z,E)-ethoxy-acrylic acid ethyl ester as light yellow oil.

MS: $(M+H)^+$ 358.0;360.0.

3-(6-Amino-3-bromo-2-methyl-phenyl)-2-ethoxy-(Z,E)-acrylic Acid Ethyl Ester 14.25 g (39.8 mmol) of 3-(3-bromo-2-methyl-6-nitro-phenyl)-2(Z,E)-ethoxy-acrylic acid ethyl ester were dissolved in 150 ml of acetic acid. 6.67 g (119.4 mmol) of iron powder were added in small portions and the reaction mixture then stirred for 16 hours. To complete the reaction, it was heated at 80° C. for another 2 hours, then cooled down to room temperature and poured into a solution of sodium hydrogen carbonate in $H_2O$. 150 ml of ethyl acetate were added and the mixture was stirred vigorously for 30 minutes, then filtered (dicalite) and extracted (two times) with ethyl acetate. The combined organic phases were washed with water, dried over magnesium sulfate and evaporated to give a crude product which was purified by chromatography (silicagel, eluent: gradient of n-heptane/ethyl acetate) to yield 7.11 g of 3-(6-amino-3-bromo-2-methyl-phenyl)-2-ethoxy-(Z,E)-acrylic acid ethyl ester as orange solid.

MS: $(M+H)^+$ 328.1;330.1.

3-(6-Acetylamino-3-bromo-2-methyl-phenyl)-2-ethoxy-(Z,E)-acrylic Acid Ethyl Ester 6.7 g (20.4 mmol) of 3-(6-amino-3-bromo-2-methyl-phenyl)-2-ethoxy-(Z,E)-acrylic acid ethyl ester were dissolved in 100 ml of dichloromethane; then, 7.11 ml (51.0 mmol) of triethyl amine were added while stirring. The mixture was subsequently cooled down to 5° C. and 1.61 ml (22.5 mmol) of acetyl chloride were added drop by drop. It was then warmed up to ambient temperature. After stirring for 90 minutes, the reaction mixture was poured into ice water and extracted 3 times with dichloromethane. The combined organic phases were washed with water, dried over magnesium sulfate and evaporated to give a crude product which was purified by chromatography (silicagel, eluent: gradient of n-heptane/ethyl acetate) to yield 7.76 g of 3-(6-acetylamino-3-bromo-2-methyl-phenyl)-2-ethoxy-(Z,E)-acrylic acid ethyl ester as light yellow oil.

MS: $(M-C_2H_5)^+$ 340.0;342.0.

5-Bromo-4-methyl-1H-indole-2-carboxylic Acid Ethyl Ester 7.63 g (20.6 mmol) of 3-(6-acetylamino-3-bromo-2-methyl-phenyl)-2-ethoxy-(Z,E)-acrylic acid ethyl ester were dissolved in 300 ml of toluene; then, 0.36 g (2.06 mmol) p-toluene sulfonic acid were added and the reaction mixture was stirred for 18 hours at reflux. After evaporation of the solvent, the residue was dissolved in dichloromethane, water was added and the pH adjusted to pH 8–9. Then, the mixture was extracted 3 times with dichloromethane. The combined organic phases were washed with water, dried over magnesium sulfate and evaporated to give 5.43 g of crude 5-bromo-4-methyl-]H-indole-2-carboxylic acid ethyl ester as light yellow solid.

MS: (M)$^+$ 281.0; 283.0.

5-Bromo-4-methyl-1H-indole-2-carboxylic Acid 5.37 g (19.0 mmol) of 5-bromo-4-methyl-1H-indole-2-carboxylic acid ethyl ester were dissolved in 150 ml of dioxane; then, 38.1 ml (38.1 mmol) of a lithium hydroxide solution (1 molar in water) were added and the reaction mixture was stirred for 60 hours at room temperature. After evaporation of the solvents, the residue was dissolved in dichloromethane; water was added and the pH adjusted to pH 2–3; then, the mixture was extracted 3 times with dichloromethane. The combined organic phases were washed with water, dried over magnesium sulfate and evaporated to give 4.82 g of crude 5-bromo-4-methyl-1H-indole-2-carboxylic acid as off-white solid.

MS: (M–H)$^-$ 252.0; 254.0.

4-Methyl-1H-indole-5-carbonitrile 4.71 g (18.5 mmol) of 5-bromo-4-methyl-1H-indole-2-carboxylic acid and 5.03 g (56.2 mmol) of cuprous cyanide were dissolved in 35 ml of quinoline and the solution heated at 230° C. for 90 minutes. The reaction mixture was then cooled down to ambient temperature and poured onto crashed ice. The pH was adjusted to pH 2–3 and the mixture subsequently extracted 3 times with ether. The combined organic phases were washed with water, dried over magnesium sulfate and evaporated to give a crude product which was purified by chromatography (silicagel, eluent: gradient of n-heptane/ethyl acetate) to yield 2.36 g of 4-methyl-1H-indole-5-carbonitrile as light brown solid.

MS: (M+H)$^+$ 157.2.

4-Methyl-1H-indole-5-carbaldehyde

In analogy to the procedure described in preparation 5a), 4-methyl-1H-indole-5-carbonitrile was reacted with sodium hypophosphite monohydrate and Raney-Nickel in acetic acid/pyridine to give 4-methyl-1H-indole-5-carbaldehyde as light yellow solid.

MS: (M+H)$^+$ 160.2.

Rac-2-Ethoxy-3-(4-methyl-1H-indol-5-yl)-propionic Acid Ethyl Ester

In analogy to the procedures described in preparation 1a) and 1b), 4-methyl-1H-indole-5-carbaldehyde was reacted with (1,2-diethoxy-2-oxoethyl)triphenyl phosphonium chloride in dichloromethane in the presence of tetramethyl guanidine to give (Z,E)-2-ethoxy-3-(4-methyl-1H-indol-5-yl)-acrylic acid ethyl ester, which was subsequently hydrogenated to yield the title compound as light brown solid.

MS: (M+NH$_4$)$^+$ 293.2.

Preparation 11

Rac-2-Ethoxy-3-(1H-indol-6-yl)-propionic Acid Ethyl Ester

In analogy to the procedures described in preparation 1a) and 1b), 1H-indole-6-carbaldehyde was reacted with (1,2-diethoxy-2-oxoethyl)triphenyl phosphonium chloride in dichloromethane in the presence of tetramethyl guanidine to give (Z,E)-2-ethoxy-3-(1H-indol-6-yl)-acrylic acid ethyl ester, which was subsequently hydrogenated to yield the title compound as colorless solid.

MS: (M+H)$^+$ 262.2.

Preparation of Final Compounds

General Description for the Alkylation of the Indoles Followed by In Situ Hydrolysis Examples 1–32, 34

To a solution of 1 mmol of the indole in 7 ml of DMSO was added at 22° C. 4 mmol of powdered KOH, stirring was continued for 15 min which was followed by the addition of a solution of 1.7 mmol of the chloride or mesylate in 1 ml of DMSO and stirring was continued until the conversion was complete (overnight). The dark mixture was acidified to pH=3 using formic acid followed by partitioning between AcOEt and saturated aqueous NH$_4$Cl. The aqueous layer was extracted several times with AcOEt and the organic layers were washed several times with water. The combined organic layers were dried, evaporated and the residue was chromatographed on silica or on RP-18 using AcOEt/n-hexane or CH$_3$CN/H$_2$O, respectively, of various ratios to give the compounds characterized in the following examples.

Example 1

Rac-2-Ethoxy-3-[1-(5-methyl-2-phenyl-oxazol-4-ylmethyl)-1H-indol-5-yl]-propionic Acid Starting from rac-2-ethoxy-3-(1H-indol-5-yl)-propionic acid ethyl ester and 4-chloromethyl-2-phenyl-5-methyl-oxazole, the title compound was obtained in 64% yield as a pale yellow solid. MS: (M–H)$^-$ 403.3.

Example 2

(S)-2-Ethoxy-3-[1-(5-methyl-2-phenyl-oxazol-4-ylmethyl)-1H-indol-5-yl]-propionic Acid Starting from (S)-2-ethoxy-3-(1H-indol-5-yl)-propionic acid methyl ester and 4-chloromethyl-2-phenyl-5-methyl-oxazole, the title compound was obtained in 64% yield as a colourless oil. MS: (M–H)$^-$ 403.3.

Example 3

Rac-2-Ethoxy-3-{1-[2-(2-fluoro-phenyl)-5-methyl-oxazol-4-ylmethyl]-1H-indol-5-yl}-propionic Acid Starting from rac-2-ethoxy-3-(1H-indol-5-yl)-propionic acid ethyl ester and 4-chloromethyl-2-(2-fluoro-phenyl)-5-methyl-oxazole, the title compound was obtained in 47% yield as a yellow solid. MS: (M+H)$^+$ 423.3.

Example 4

Rac-3-{1-[2-(2-Chloro-phenyl)-5-methyl-oxazol-4-ylmethyl]-1H-indol-5-yl}-2-propionic Acid Starting from rac-2-ethoxy-3-(1H-indol-5-yl)-propionic acid ethyl ester and 4-chloromethyl-2-(2-chloro-phenyl)-5-methyl-oxazole, the title compound was obtained in 31% yield as a yellow solid. MS: (M+H)$^+$ 439.3.

Example 5

(S)-3-{1-[2-(2-Chloro-phenyl)-5-methyl-oxazol-4-ylmethyl]-1H-indol-5-yl}-2-ethoxy-propionic Acid Starting from (S)-2-ethoxy-3-(1H-indol-5-yl)-propionic acid methyl ester and 4-chloromethyl-2-(2-chloro-phenyl)-5-methyl-oxazole, the title compound was obtained in 56% yield as a pale brown amorphous solid. MS: (M–H)$^-$ 437.2.

Example 5a

Alternative Preparation of (S)-3-{1-[2-(2-Chloro-phenyl)-5-methyl-oxazol-4-ylmethyl]-1H-indol-5-yl}-2-ethoxy-propionic Acid In a glove box (O$_2$ content≦2 ppm), a 185 ml stainless steel autoclave was charged with 3.0 g of (Z)-3-{1-[2-(2-chloro-phenyl)-5-methyl-oxazol-4-ylmethyl]-1H-indol-5-yl}-2-ethoxy-acrylic acid (example 69) (6.9 mmol), 10 ml of dichloromethane, 10 ml of methanol, 0.7 ml of a 30% solution of NaOMe (3.6 mmol) in methanol and 11.8 mg of

[Ru(OAc)₂((+)-TMBTP)] (0.015 mmol). TMBTP is 4,4'-bis (diphenylphosphino)-2,2',5,5'-tetramethyl-3,3'-dithiophene, its synthesis as (R) or (S) enantiomer is described in WO 96/01831 appl to Italfarmaco Sud and in T. Benincori et al., *J. Org. Chem.* 2000, 65, 2043. The complex [Ru(OAc)₂((+)-TMBTP)] has been synthesized in analogy to a general procedure reported in N. Peiken et al., *Organonmetallics* 1997, 16, 537, $^{31}$P-NMR (CDCl₃): δ 1.4 ppm (s). The autoclave was sealed and the hydrogenation was run under stirring at 40° C. under 60 bar of hydrogen. After 16 h the autoclave was opened and the yellow-brown solution was rotary evaporated to dryness (50° C./5 mbar). The residue was dissolved in 40 ml of ethyl acetate and 40 ml of water. The aqueous layer was acidified (pH 3–4) with aqueous hydrochloric acid (25%). The organic layer was separated and evaporated to dryness (50° C./5 mbar) to afford 3.8 g of crude product as an orange oil with an enantiomeric purity of 92% and a chemical purity of >98% according to HPLC; for a detailed description of the method used for the enantiomeric purity (ee) determination see below. Crude product from 71.5 g (163 mmol) (Z)-3-{1-[2-(2-chloro-phenyl)-5-methyl-oxazol-4-ylmethyl]-1H-indol-5-yl}-2-ethoxy-acrylic acid (example 69) produced in several hydrogenation experiments similar to that just described, were dissolved in 1000 ml of dichloromethane, (S)-phenylethylamine (21.20 ml, 163 mmol) was added and the solvent removed under reduced pressure. The light beige residue was crystallized from 1500 ml ethyl acetate to yield after washing twice with 250 ml heptane/ethyl acetate (4:1) and drying in vacuo 73.14 g (131 mmol, 80.1%) of colorless crystals with an enantiomeric purity (ee) of 97.6% with respect to the title acid. 72.5 g (129 mmol) of these crystals were suspended in ice water/ethyl acetate 1/1. The pH of the suspension was adjusted to 1 with concentrated aqueous hydrochloric acid, the layers were separated and the aqueous layer extracted two more times with ethyl acetate. The combined extracts were washed with ice water, dried over magnesium sulfate and the solvent removed in vacuo to obtain colorless crystals which were recrystallized from ethyl acetate/n-heptane to afford 47.4 g (108 mmol, 83.7%) of the title compound as colorless crystals showing 98.3% ee according to chiral HPLC: Melting point: 97° C.

HPLC method for ee and purity determination: Chiralpak-ADH column No. CE114, 25 cm×4.6 mm, 90% heptane/10% ethanol with 1% trifluoroacetic acid, flow at 0.8 ml/min, 25° C., 275 nm. Retention times: S-acid 16.5 min., R-acid 19.5 min., α,β-unsaturated Z-acid 48.1 min.

Example 6

Rac-2-Ethoxy-3-[1-(5-methyl-2-o-tolyl-oxazol-4-ylmethyl)-1H-indol-5-yl]-propionic Acid Starting from rac-2-ethoxy-3-(1H-indol-5-yl)-propionic acid ethyl ester and 4-chloromethyl-5-methyl-2-o-tolyl-oxazole, the title compound was obtained in 43% yield as a pale brown solid. MS: (M+H)⁺ 419.3.

Example 7

Rac-2-Ethoxy-3-{1-[2-(2-methoxy-phenyl)-5-methyl-oxazol-4-ylmethyl]-1H-indol-5-yl}-propionic Acid Starting from rac-2-ethoxy-3-(1H-indol-5-yl)-propionic acid ethyl ester and 4-chloromethyl-2-(2-methoxy-phenyl)-5-methyl-oxazole, the title compound was obtained in 56% yield as a pale yellow solid. MS: (M+H)⁺ 435.3.

Example 8

(S)-2-Ethoxy-3-{1-[2-(2-methoxy-phenyl)-5-methyl-oxazol-4-ylmethyl]-1H-indol-5-yl}-propionic Acid Starting from (S)-2-ethoxy-3-(1H-indol-5-yl)-propionic acid methyl ester and 4-chloromethyl-2-(2-methoxy-phenyl)-5-methyl-oxazole, the title compound was obtained in 66% yield as a pale yellow solid. MS: (M–H)⁻ 433.2.

Example 8a

Alternative Preparation of (S)-2-Ethoxy-3-{1-[2-(2-methoxy-phenyl)-5-methyl-oxazol-4-ylmethyl]-1H-indol-5-yl}-propionic Acid a) (Z)-2-Ethoxy-3-{1-[2-(2-methoxy-phenyl)-5-methyl-oxazol-4-ylmethyl]-1H-indol-5-yl}-acrylic Acid In analogy to the procedures described in examples 36a) and 36b), (Z)-2-ethoxy-3-(1H-indol-5-yl)-acrylic acid ethyl ester [preparation 1a)] was reacted with 4-chloromethyl-2-(2-methoxy-phenyl)-5-methyl-oxazole to give (Z)-2-ethoxy-3-{1-[2-(2-methoxy-phenyl)-5-methyl-oxazol-4-ylmethyl]-1H-indol-5-yl}-acrylic acid ethyl ester, which was subsequently saponified to yield (Z)-2-ethoxy-3-{1-[2-(2-methoxy-phenyl)-5-methyl-oxazol-4-ylmethyl]-1H-indol-5-yl}-acrylic acid as colorless solid.

b) (S)-2-Ethoxy-3-{1-[2-(2-methoxy-phenyl)-5-methyl-oxazol-4-ylmethyl]-1H-indol-5-yl}-propionic Acid In analogy to the procedure described in example 5a, 0.5 g of (Z)-2-ethoxy-3-{1-[2-(2-methoxy-phenyl)-5-methyl-oxazol-4-ylmethyl]-1H-indol-5-yl}-acrylic acid (1.2 mmol), dissolved in 7 ml of ethanol containing 0.1 ml of a 30% aqueous NaOH solution (0.6 mmol), were hydrogenated in a 35 ml stainless steel autoclave for 16 h at 60 bar of hydrogen at 40° C. using 46.8 mg of the [Ru(OAc)₂((+)-TMBTP)]-catalyst (0.06 mmol) to yield after work-up 1.1 g of crude product as a brown solid with an enantiomeric purity of 93% and a chemical purity of >98% according to HPLC; for a detailed description of the method used for the enantiomeric purity (ee) determination see below. Crude product from 2.64 g (6.11 mmol) (Z)-2-ethoxy-3-{1-[2-(2-methoxy-phenyl)-5-methyl-oxazol-4-ylmethyl]-1H-indol-5-yl}-acrylic acid in total produced in several hydrogenation experiments similar to that just described, were purified by column chromatography (silica gel, hexane/ethyl acetate (1:1), two times) yielding 1.81 g of a beige foam. The foam was dissolved in hot ethyl acetate, charcoal (360 mg) was added and the mixture was heated under reflux conditions for 10 min. Then, the charcoal was filtered off and the product was allowed to crystallize after addition of n-hexane to afford the title compound (1.47 g, 3.38 mmol, 55.3%) as an off-white solid showing 94% ee according to chiral HPLC. Melting point: 59–60° C.

HPLC method for ee and purity determination: Chiralcel-OJH column Nr. CE024, 25 cm×4.6 mm, 80% heptane/20% ethanol with 1.5% trifluoroacetic acid, flow at 0.8 ml/min, 25° C., 280 nm. Retention times: R-acid 23.8 min., S-acid 28.3 min., α,β-unsaturated Z-acid 44.8 nm.

Example 9

Rac-2-Ethoxy-3-{1-[2-(2-isopropoxy-phenyl)-5-methyl-oxazol-4-ylmethyl]-1H-indol-5-yl}-propionic Acid Starting from rac-2-ethoxy-3-(1H-indol-5-yl)-propionic acid ethyl ester and 4-chloromethyl-2-(2-isopropoxy-phenyl)-5-methyl-oxazole, the title compound was obtained in 60% yield as a brown oil. MS: (M+H)⁺ 463.3.

Example 10

Rac-3-{1-[2-(3-Chloro-phenyl)-5-methyl-oxazol-4-ylmethyl]-1H-indol-5-yl}-2-ethoxy-propionic Acid Starting from rac-2-ethoxy-3-(1H-indol-5-yl)-propionic acid ethyl ester and 4-chloromethyl-2-(3-chloro-phenyl)-5-methyl-oxazole, the title compound was obtained in 21% yield as a yellow solid. MS: (M+H)⁺ 439.3.

Example 11
Rac-2-Ethoxy-3-{1-[2-(4-ethyl-phenyl)-5-methyl-oxazol-4-ylmethyl]-1H-indol-5-yl}-propionic Acid Starting from rac-2-ethoxy-3-(1H-indol-5-yl)-propionic acid ethyl ester and 4-chloromethyl-2-(4-ethyl-phenyl)-5-methyl-oxazole, the title compound was obtained in 41% yield as a yellow solid. MS: (M+H)$^+$ 433.4.

Example 12
(S)-2-Ethoxy-3-{1-[2-(4-ethyl-phenyl)-5-methyl-oxazol-4-ylmethyl]-1H-indol-5-yl}-propionic Acid Starting from (S)-2-ethoxy-3-(1H-indol-5-yl)-propionic acid methyl ester and 4-chloromethyl-2-(4-ethyl-phenyl)-5-methyl-oxazole, the title compound was obtained in 47% yield as a colourless solid. MS: (M−H)$^-$ 431.3.

Example 13
(R)-2-Ethoxy-3-{1-[2-(4-ethyl-phenyl)-5-methyl-oxazol-4-ylmethyl]-1H-indol-5-yl}-propionic Acid Starting from (R)-2-ethoxy-3-(1H-indol-5-yl)-propionic acid ethyl ester and 4-chloromethyl-2-(4-ethyl-phenyl)-5-methyl-oxazole, the title compound was obtained in 60% yield as a pale yellow solid. AS: (M−H)$^-$ 431.2.

Example 14
Rac-2-Ethoxy-3-1-[2-(4-isopropyl-7phenyl)-5-methyl-oxazol-4-ylmethyl]-1H-indol-5-yl}-propionic Acid Starting from rac-2-ethoxy-3-(1H-indol-5-yl)-propionic acid ethyl ester and 4-chloromethyl-2-(4-isopropyl-phenyl)-5-methyl-oxazole, the title compound was obtained in 48% yield as a yellow solid. MS: (M+H)$^+$ 447.4.

Example 15
Rac-1-{[2-(4-tert-Butyl-phenyl)-5-methyl-oxazol-4-ylmethyl]-1H-indol-5-yl}-2-ethoxy-propionic Acid Starting from rac-2-ethoxy-3-(1H-indol-5-yl)-propionic acid ethyl ester and 4-chloromethyl-2-(4-tert-butyl-phenyl)-5-methyl-oxazole, the title compound was obtained in 50% yield as a brown oil. MS: (M+H)$^+$ 461.3.

Example 16
Rac-2-Ethoxy-3-{1-[2-(4-fluoro-phenyl)-5-methyl-oxazol-4-ylmethyl]-1H-indol-5-yl}-propionic Acid Starting from rac-2-ethoxy-3-(1H-indol-5-yl)-propionic acid ethyl ester and 4-chloromethyl-2-(4-fluoro-phenyl)-5-methyl-oxazole, the title compound was obtained in 39% yield as a colourless solid. MS: (M+H)$^{30}$ 423.3.

Example 17
Rac-2-Ethoxy-3-{1-[5-methyl-2-(4-trifluoromethyl-phenyl)-oxazol-4-ylmethyl]-1H-indol 5-yl}-propionic Acid Starting from rac-2-ethoxy-3-(1H-indol-5-yl)-propionic acid ethyl ester and 4-chloromethyl-5-methyl-2-(4-trifluoromethyl-phenyl)-oxazole, the title compound was obtained in 27% yield as a yellow solid. MS: (M+H)$^+$ 473.2.

Example 18
(S)-2-Ethoxy-3-{1-[5-methyl-2-(4-trifluoromethyl-phenyl)-oxazol-4-ylmethyl]-1H-indol-5-yl}-propionic Acid Starting from (S)-2-ethoxy-3-(1H-indol-5-yl)-propionic acid methyl ester and 4-chloromethyl-5-methyl-2-(4-trifluoromethyl-phenyl)-oxazole, the title compound was obtained in 50% yield as a pale yellow solid. MS: (M−H)$^-$ 471.1.

Example 19
Rac-3-{1-[2-(3,5-Dimethyl-phenyl)-5-methyl-oxazol-4-ylmethyl]-1H-indol-5-yl}-2-ethoxy-propionic Acid Starting from rac-2-ethoxy-3-(1H-indol-5-yl)-propionic acid ethyl ester and 4-chloromethyl-2-(3,5-dimethyl-phenyl)-5-methyl-oxazole, the title compound was obtained in 45% yield as a pale yellow solid. MS: (M+H)$^+$ 433.4.

Example 20
Rac-3-{1-[2-(3,5-Dimethoxy-phenyl)-5-methyl-oxazol-4-ylmethyl]-1H-indol-5-yl}-2-ethoxy-propionic Acid Starting from rac-2-ethoxy-3-(1H-indol-5-yl)-propionic acid ethyl ester and 4-chloromethyl-2-(3,5-dimethoxy-phenyl)-5-methyl-oxazole, the title compound was obtained in 50% yield as a colourless solid. MS: (M−H)$^-$ 463.2.

Example 21
(S)-3-{1-[2-(3,5-Dimethoxy-phenyl)-5-methyl-oxazol-4-ylmethyl]-1H-indol-5-yl}-2-ethoxy-propionic Acid Starting from (S)-2-ethoxy-3-(1H-indol-5-yl)-propionic acid methyl ester and 4-chloromethyl-2-(3,5-dimethoxy-phenyl)-5-methyl-oxazole, the title compound was obtained in 43% yield as a pale red solid. MS: (M−H)$^-$ 463.2.

Example 22
Rac-3-{1-[2-(3,5-Difluoro-phenyl)-5-methyl-oxazol-4-ylmethyl]-1H-indol-5-yl}-2-ethoxy-propionic Acid Starting from rac-2-ethoxy-3-(1H-indol-5-yl)-propionic acid ethyl ester and 4-chloromethyl-2-(3,5-difluoro-phenyl)-5-methyl-oxazole, the title compound was obtained in 20% yield as a brown oil. MS: (M+H)$^+$ 441.3.

Example 23
Rac-3-{1-[2-(3,5-Dichloro-phenyl)-5-methyl-oxazol-4-ylmethyl]-1H-indol-5-yl}-2-ethoxy-propionic Acid Starting from rac-2-ethoxy-3-(1H-indol-5-yl)-propionic acid ethyl ester and 4-chloromethyl-2-(3,5-dichloro-phenyl)-5-methyl-oxazole, the title compound was obtained in 4% yield as a pale yellow solid. MS: (M+H)$^+$ 473.1 and 475.2.

Example 24
Rac-2-Ethoxy-3-{1-[2-(4-fluoro-3-methyl-phenyl)-5-methyl-oxazol-4-ylmethyl]-1H-indol-5-yl}-propionic Acid Starting from rac-2-ethoxy-3-(1H-indol-5-yl)-propionic acid ethyl ester and 4-chloromethyl-2-(4-fluoro-3-methyl-phenyl)-5-methyl-oxazole, the title compound was obtained in 48% yield as a colourless solid. MS: (M+H)$^+$ 437.3.

Example 25
(S)-2-Ethoxy-3-{1-[2-(4-fluoro-3-methyl-phenyl)-5-methyl-oxazol-4-ylmethyl]-1H-indol-5-yl}-propionic Acid Starting from (S)-2-ethoxy-3-(1H-indol-5-yl)-propionic acid methyl ester and 4-chloromethyl-2-(4-fluoro-3-methyl-phenyl)-5-methyl-oxazole, the title compound was obtained in 58% yield as a pale yellow solid. MS: (M−H)$^-$ 435.2.

Example 26
Rac-2-Ethoxy-3-[1-(5-methyl-2-thiophen-2-yl-oxazol-4-ylmethyl)-1H-indol-5-yl]-propionic Acid Starting from rac-2-ethoxy-3-(1H-indol-5-yl)-propionic acid ethyl ester and 4-chloromethyl-5-methyl-2-thiophen-2-yl-oxazole, the title compound was obtained in 31% yield as a yellow solid. MS: (M+H)$^+$ 411.2.

Example 27
Rac-2-Ethoxy-3-{1-[2-(3,4,5-trimethoxy-phenyl)-5-methyl-oxazol-4-ylmethyl]-1H-indol-5-yl}-propionic Acid Starting from rac-2-ethoxy-3-(1H-indol-5-yl)-propionic acid ethyl ester and 4-chloromethyl-5-methyl-2-(3,4,5-trimethoxy-phenyl)-oxazole, the title compound was obtained in 3% yield as a white solid. MS: (M+H)$^+$ 495.2.

Example 28
Rac-2-Ethoxy-3-[1-(2-phenyl-oxazol-4-ylmethyl)-1H-indol-5-yl]-propionic Acid Starting from rac-2-ethoxy-3-(1H-indol-5-yl)-propionic acid ethyl ester and 4-chloromethyl-2-phenyl-oxazole, the title compound was obtained in 80% yield as a brown oil. MS: (M+H)$^+$ 391.1.

Example 29
Rac-2-Ethoxy-3-[1-(2-phenyl-thiazol-4-ylmethyl)-1H-indol-5-yl 1-propionic Acid Starting from rac-2-ethoxy-3-(1H-indol-5-yl)-propionic acid ethyl ester and 4-chloromethyl-2-phenyl-thiazole, the title compound was obtained in 64% yield as a brown oil. MS: (M+H)$^+$ 407.3.

Example 30
Rac-2-Ethoxy-3-[1-(5-methyl-2-phenyl-thiazol-4-ylmethyl)-1H-indol-5-yl]-propionic Acid Starting from rac-2-ethoxy-3-(1H-indol-5-yl)-propionic acid ethyl ester and 4-bromomethyl-5-methyl-2-phenyl-thiazole, the title compound was obtained in 1% yield as a yellow oil. MS: (M+H)$^+$ 421.2.

Example 31
Rac-3-1-[2-(4-Chloro-phenyl)-thiazol-4-ylmethyl]-1H-indol-5-yl-2-ethoxy-propionic Acid Starting from rac-2-ethoxy-3-(1H-indol-5-yl)-propionic acid ethyl ester and 4-(chloromethyl)-2-(p-chlorophenyl)thiazole, the title compound was obtained in 23% yield as a brown oil. MS: (M+H)$^+$ 441.3.

Example 32
(Z)-2-Methoxy-3-[1-(5-methyl-2-phenyl-oxazol-4-ylmethyl)-1H-indol-5-yl]-acrylic Acid Starting from (Z)-3-(1H-indol-5-yl)-2-methoxy-acrylic acid benzyl ester and 4-chloromethyl-2-phenyl-5-methyl-oxazole, the title compound was obtained in 75% yield as an off-white solid. MS: (M+H)$^+$ 389.2.

Example 33
Rac-2-Methoxy-3-[1-(5-methyl-2-phenyl-oxazol-4-ylmethyl)-1H-indol-5-yl]-propionic Acid A suspension of 80 mg of (Z)-2-methoxy-3-[1-(5-methyl-2-phenyl-oxazol-4-ylmethyl)-1H-indol-5-yl]-acrylic acid in 5 ml of methanol and 2 ml of dichloromethane and 30 mg of Pd/C 10%) was hydrogenated at 22° C. and 1 bar until hydrogen uptake ceased (3 h). The mixture was filtered, the filtrate evaporated and the residue was purified by preparative HPLC (RP-18, CH$_3$CN/H$_2$O, gradient) to give 49 mg of the title compound as a yellow oil. MS: (M–H)$^-$ 389.1.

Example 34
(Z)-2-Methoxy-3-{1-[2-(5-methyl-2-phenyl-oxazol-4-yl)-ethyl]-1H-indol-5-yl}Acid Starting from (Z)-3-(1H-indol-5-yl)-2-methoxy-acrylic acid benzyl ester and methanesulfonic acid 2-(5-methyl-2-phenyl-oxazol-4-yl)-ethyl ester, the title compound was obtained in 5% yield as a colourless solid. MS: (M+H)$^+$ 403.4.

Example 35
Rac-2-Methoxy-3-{1-[2-(5-methyl-2-phenyl-oxazol-4-yl)-ethyl]-1H-indol-5-yl}-propionic Acid A suspension of 9 mg of (Z)-2-Methoxy-3-{1-[2-(5-methyl-2-phenyl-oxazol-4-yl)-ethyl]-1H-indol-5-yl}-acrylic acid in 2 ml of methanol and 1 ml of dichloromethane and 6 mg of Pd/C 10%) was hydrogenated at 22° C. and 1 bar until hydrogen uptake ceased (2 h). The mixture was filtered, the filtrate evaporated and the residue was purified by HPLC (RP-18, CH$_3$CN/H$_2$O, gradient) to give 7 mg of the title compound as a colorless oil. MS: (M–H)$^-$ 403.3.

Example 36
Rac-2-Ethoxy-3-{1-[2-(4-isopropyl-phenyl)-5-methyl-oxazol-4-ylmethyl]-3-methyl-1H-indol-5-yl}-propionic Acid Rac-2-Ethoxy-3-{1-[2-(4-isopropyl-phenyl)-5-methyl-oxazol-4-ylmethyl]-3-methyl-1H-indol-5-yl}-propionic Acid Ethyl Ester 0.28 g (1.0 mmol) rac-2-ethoxy-3-(3-methyl-1H-indol-5-yl)-propionic acid ethyl ester (preparation 4) and 0.30 g (1.2 mmol) 4-chloromethyl-2-(4-isopropyl-phenyl)-5-methyl-oxazole were dissolved under argon in 5.0 ml N,N-dimethylformamide; 0.048 g (1.1 mmol) sodium hydride (55% in mineral oil) were added and the reaction mixture then stirred for 48 hours at ambient temperature. It was then diluted with water and extracted with ether. The combined organic phases were dried over MgSO$_4$ and evaporated. The residue formed was purified by flash-chromatography (silica gel; eluent: gradient of hexane and ethyl acetate) to give 0.32 g (67%) of rac-2-ethoxy-3-{1-[2-(4-isopropyl-phenyl)-5-methyl-oxazol-4-ylmethyl]-3-methyl-1H-indol-5-yl}-propionic acid ethyl ester as colorless oil.

MS: (M+H)$^+$ 489.5.

Rac-2-Ethoxy-3-{1-[2-(4-isopropyl-phenyl)-5-methyl-oxazol-4-ylmethyl]-3-methyl-1H-indol-5-yl}-propionic Acid rac-2-Ethoxy-3-1-[2-(4-isopropyl-phenyl)-5-methyl-oxazol-4-ylmethyl]-3-methyl-1H-indol-5-yl}-propionic acid ethyl ester (310 mg, 0.63 mmol) were dissolved in 5 ml of dioxane; 0.95 ml of LiOH-solution (1N in water) were then added slowly at room temperature. The resulting mixture was stirred for 48 hours at room temperature and then poured onto ice, neutralized to pH 4 with HCl (1N) and extracted 3 times with dichloromethane. The combined organic phases were washed with water, dried over magnesium sulfate and evaporated; the crude product was purified by chromatography (silicagel, eluent: gradient of dichloromethane/methanol) to yield 210 mg (720% o) of rac-2-ethoxy-3-{1-[2-(4-isopropyl-phenyl)-5-methyl-oxazol-4-ylmethyl]-3-methyl-1H-indol-5-yl}-propionic acid as colorless solid.

MS: (M–H)$^-$ 459.4.

Example 37
Rac-2-Ethoxy-3-{3-methyl-1-[5-methyl-2-(4-trifluoromethyl-phenyl)-oxazol-4-ylmethyl]-1H-indol-5-yl]-propionic Acid In analogy to the procedures described in examples 36a) and 36b), rac-2-ethoxy-3-(3-methyl-1H-indol-5-yl)-propionic acid ethyl ester (preparation 4) was reacted with 4-chloromethyl-5-methyl-2-(4-trifluoromethyl-phenyl)-oxazole to give rac-2-ethoxy-3-{3-methyl-1-[5-methyl-2-(4-trifluoromethyl-phenyl)-oxazol-4-ylmethyl]-1H-indol-5-yl}-propionic acid ethyl ester, which was subsequently saponified to yield the title compound as colorless oil.

MS: (M–H)$^-$ 485.4.

Example 38
Rac-3-{1-[2-(2-Chloro-phenyl)-5-methyl-oxazol-4-ylmethyl]-3-methyl-1H-indol-5-yl}-2-ethoxy-propionic Acid In analogy to the procedures described in examples 36a) and 36b), rac-2-ethoxy-3-(3-methyl-1H-indol-5-yl)-propionic acid ethyl ester (preparation 4) was reacted with 4-chloromethyl-2-(2-chloro-phenyl)-5-methyl-oxazole to give rac-3-{1-[2-(2-chloro-phenyl)-5-methyl-oxazol-4-ylmethyl]-3-methyl-1H-indol-5-yl}-2-ethoxy-propionic acid ethyl ester, which was subsequently saponified to yield the title compound as colorless solid.

MS: (M−H)⁻ 451.2.

Example 39
Rac-2-Ethoxy-3-{1-[2-(4-fluoro-3-methyl-phenyl)-5-methyl-oxazol-4-ylmethyl]-3-methyl-1H-indol-5-yl}-propionic Acid In analogy to the procedures described in examples 36a) and 36b), rac-2-ethoxy-3-(3-methyl-1H-indol-5-yl)-propionic acid ethyl ester (preparation 4) was reacted with 4-chloromethyl-2-(4-fluoro-3-methyl-phenyl)-5-methyl-oxazole to give rac-2-ethoxy-3-{1-[2-(4-fluoro-3-methyl-phenyl)-5-methyl-oxazol-4-ylmethyl]-3-methyl-1H-indol-5-yl}-propionic acid ethyl ester, which was subsequently saponified to yield the title compound as colorless solid.

MS: (M−H)⁻ 449.3.

Example 40
Rac-2-Ethoxy-3-{2-methyl-1-[5-methyl-2-(4-trifluoromethyl-phenyl)-oxazol-4-ylmethyl]-1H-indol-5-yl}-propionic Acid In analogy to the procedures described in examples 36a) and 36b), rac-2-ethoxy-3-(2-methyl-1H-indol-5-yl)-propionic acid ethyl ester (preparation 5) was reacted with 4-chloromethyl-5-methyl-2-(4-trifluoromethyl-phenyl)-oxazole to give rac-2-ethoxy-3-{2-methyl-1-[5-methyl-2-(4-trifluoromethyl-phenyl)-oxazol-4-ylmethyl]-1H-indol-5-yl}-propionic acid ethyl ester, which was subsequently saponified to yield the title compound as colorless oil.

MS: (M−H)⁻ 485.4.

Example 41
Rac-2-Ethoxy-3-{-[2-(4-isopropyl-phenyl)-5-methyl-oxazol-4-ylmethyl]-2-methyl-1H-indol-5-yl}-propionic Acid In analogy to the procedures described in examples 36a) and 36b), rac-2-ethoxy-3-(2-methyl-1H-indol-5-yl)-propionic acid ethyl ester (preparation 5) was reacted with 4-chloromethyl-2-(4-isopropyl-phenyl)-5-methyl-oxazole to give rac-2-ethoxy-3-{1-[2-(4-isopropyl-phenyl)-5-methyl-oxazol-4-ylmethyl]-2-methyl-1H-indol-5-yl}-propionic acid ethyl ester, which was subsequently saponified to yield the title compound as colorless oil.

MS: (M−H)⁻ 459.4.

Example 42
Rac-2-Ethoxy-3-{1-[2-(4-fluoro-3-methyl-phenyl)-5-methyl-oxazol-4-ylmethyl]-2-methyl-1H-indol-5-yl}-propionic Acid In analogy to the procedures described in examples 36a) and 36b), rac-2-ethoxy-3-(2-methyl-1H-indol-5-yl)-propionic acid ethyl ester (preparation 5) was reacted with 4-chloromethyl-2-(4-fluoro-3-methyl-phenyl)-5-methyl-oxazole to give rac-2-ethoxy-3-1{-[2-(4-fluoro-3-methyl-phenyl)-5-methyl-oxazol-4-ylmethyl]-2-methyl-1H-indol-5-yl}-propionic acid ethyl ester, which was subsequently saponified to yield the title compound as colorless oil.

MS: (M+H)⁺ 451.3

Example 43
Rac-3-{1-[2-(2-Chloro-phenyl)-5-methyl-oxazol-4-ylmethyl]-2-methyl-1H-indol-5-yl}-2-ethoxy-propionic Acid In analogy to the procedures described in examples. 36a) and 36b), rac-2-ethoxy-3-(2-methyl-1H-indol-5-yl)-propionic acid ethyl ester (preparation 5) was reacted with 4-chloromethyl-2-(2-chloro-phenyl)-5-methyl-oxazole to give rac-3-{1-[2-(2-chloro-phenyl)-5-methyl-oxazol-4-ylmethyl]-2-methyl-1H-indol-5-yl}-2-ethoxy-propionic acid ethyl ester, which was subsequently saponified to yield the title compound as colorless solid.

MS: (M−H)⁻ 451.2

Example 44
Rac-2-Ethoxy-3-[2-methyl-1-(2-phenyl-thiazol-4-ylmethyl)-1H-indol-5-yl]-propionic Acid 0.28 g (1.0 mmol) rac-2-ethoxy-3-(2-methyl-1H-indol-5-yl)-propionic acid ethyl ester (preparation 5) were reacted with 0.23 g (1.1 mmol) 4-chloromethyl-2-phenyl-thiazole in 5 ml N,N-dimethylformamide in the presence of 0.09 g (2.0 mmol) sodium hydride (55%) in mineral oil) at room temperature for 16 hours. The reaction mixture was then diluted with water and extracted with dichloromethane. The combined organic phases were dried over MgSO₄ and evaporated. The residue formed was purified by flash-chromatography (silica gel; eluent: gradient of n-heptane and ethyl acetate) to give 0.38 g (90%) of rac-2-ethoxy-3-[2-methyl-1-(2-phenyl-thiazol-4-ylmethyl)-1H-indol-5-yl]-propionic acid as light brown solid.

MS: (M−H)⁻ 419.2.

Example 45
Rac-3-{1-[2-(4-tert-Butyl-phenyl)-oxazol-4-ylmethyl 1–2-methyl-1H-indol-5-yl}-2-ethoxy propionic Acid In analogy to the procedure described in example 44, rac-2-ethoxy-3-(2-methyl-1H-indol-5-yl)-propionic acid ethyl ester (preparation 5) was reacted with 2-(4-tert-butyl-phenyl)-4-chloromethyl-oxazole to give rac-3-{1-[2-(4-tert-butyl-phenyl)-oxazol-4-ylmethyl]-2-methyl-1H-indol-5-yl}-2-ethoxy-propionic acid as light brown solid.

MS: (M−H)⁻ 459.4.

Example 46
Rac-3-1-(5-Methyl-2-o-tolyl-oxazol-4ylmethyl)-1H-indol-5-yl]-2-propoxy-propionic Acid In analogy to the procedure described in example 44, rac-3-(1H-indol-5-yl)-2-propoxy-propionic acid methyl ester (preparation 6) was reacted with 4-chloromethyl-5-methyl-2-o-tolyl-oxazole to give rac-3-[1-(5-methyl-2-o-tolyl-oxazol-4-ylmethyl)-1H-indol-5-yl]-2-propoxy-propionic acid as light brown oil.

MS: (M−H)⁻ 431.3.

Example 47
Rac-3-{1-[2-(2-Methoxy-phenyl)-5-methyl-oxazol-4-ylmethyl]-1H-indol-5-yl}-2-propoxy-propionic Acid In analogy to the procedure described in example 44, rac-3-(1H-indol-5-yl)-2-propoxy-propionic acid methyl ester (preparation 6) was reacted with 4-chloromethyl-2-(2-methoxy-phenyl)-5-methyl-oxazole to give rac-3-{1-{[2-(2-methoxy-phenyl)-5-methyl-oxazol-4-ylmethyl]-1H-indol-5-yl}-2-propoxy-propionic acid as light yellow solid.

MS: (M−H)⁻ 447.3.

Example 48
Rac-3-{1-[5-Methyl-2-(4-trifluoromethyl-phenyl)-oxazol-4-ylmethyl]-1H-indol-5-yl}-2-propoxy-propionic Acid In analogy to the procedure described in example 44, rac-3-(1H-indol-5-yl)-2-propoxy-propionic acid methyl ester (preparation 6) was reacted with 4-chloromethyl-5-methyl-2-(4-trifluoromethyl-phenyl)-oxazole to give rac-3-1-[5-methyl-2-(4-trifluoromethyl-phenyl)-oxazol-4-yl methyl]-1H-indol-5-yl}-2-propoxy-propionic acid as light yellow solid.

MS: (M–H)⁻ 485.4.

Example 49
Rac-3-{1-[5-Methyl-2-(4-trifluoromethyl-phenyl)-oxazol-4-ylmethyl]-1H-indol-5-yl}-2-phenoxy-propionic Acid In analogy to the procedure described in example 44, rac-3-(1H-indol-5-yl)-2-phenoxy-propionic acid methyl ester (preparation 7) was reacted with 4-chloromethyl-5-methyl-2-(4-trifluoromethyl-phenyl)-oxazole to give rac-3-{1-[5-methyl-2-(4-trifluoromethyl-phenyl)-oxazol-4-yl methyl]-1H-indol-5-yl}-2-phenoxy-propionic acid as colorless solid.

MS: (M–H)⁻ 519.4.

Example 50
Rac-3-1-[2-(4-Isopropyl-phenyl)-5-methyl-oxazol-4-ylmethyl]-1H-indol-5-yl}-2-propoxy-propionic Acid In analogy to the procedure described in example 44, rac-3-(1H-indol-5-yl)-2-phenoxy-propionic acid methyl ester (preparation 7) was reacted with 4-chloromethyl-2-(4-isopropyl-phenyl)-5-methyl-oxazole to give rac-3-{1-[2-(4-isopropyl-phenyl)-5-methyl-oxazol-4-ylmethyl]-1H-indol-5-yl}-2-phenoxy-propionic acid as off-white solid.

MS: (M–H)⁻ 493.3

Example 51
Rac-3-{1-[2-(2-Chloro-phenyl)-5-methyl-oxazol-4-ylmethyl]-1H-indol-5-yl}-2-phenoxy-propionic Acid In analogy to the procedure described in example 44, rac-3-(1H-indol-5-yl)-2-phenoxy-propionic acid methyl ester (preparation 7) was reacted with 4-chloromethyl-2-(2-chloro-phenyl)-5-methyl-oxazole to give rac-3-{1-[2-(2-chloro-phenyl)-5-methyl-oxazol-4-ylmethyl]-1H-indol-5-yl}-2-phenoxy-propionic acid as off-white solid.

MS: (M–H)⁻ 485.3.

Example 52
Rac-3-1-[2-(4-Fluoro-3-methyl-phenyl)-5-methyl-oxazol-4-ylmethyl]-1H-indol-5-yl}-2-phenoxy-propionic Acid In analogy to the procedure described in example 44, rac-3-(1H-indol-5-yl)-2-phenoxy-propionic acid methyl ester (preparation 7) was reacted with 4-chloromethyl-2-(4-fluoro-3-methyl-phenyl)-5-methyl-oxazole to give rac-3-{1-[2-(4-fluoro-3-methyl-phenyl)-5-methyl-oxazol-4-ylmethyl]-1H-indol-5-yl}-2-phenoxy-propionic acid off-white solid.

MS: (M–H)⁻ 483.3.

Example 53
Rac-2-Isopropoxy-3-[1-(5-methyl-2-o-tolyl-oxazol-4-ylmethyl)-1H-indol-5-yl]-propionic Acid In analogy to the procedure described in example 44, rac-3-(1H-indol-5-yl)-2-isopropoxy-propionic acid methyl ester (preparation 8) was reacted with 4-chloromethyl-5-methyl-2-o-tolyl-oxazole to give rac-2-isopropoxy-3-[1-(5-methyl-2-o-tolyl-oxazol-4-ylmethyl)-1H-indol-5-yl]-propionic acid as off-white solid.

MS: (M–H)⁻ 431.3.

Example 54
Rac-2-Isopropoxy-3-{1-[2-(2-methoxy-phenyl)-5-methyl-oxazol-4-ylmethyl]-1H-indol-5-yl}-propionic Acid In analogy to the procedure described in example 44, rac-3-(1H-indol-5-yl)-2-isopropoxy-propionic acid methyl ester (preparation 8) was reacted with 4-chloromethyl-2-(2-methoxy-phenyl)-5-methyl-oxazole to give rac-2-isopropoxy-3-{1-[2-(2-methoxy-phenyl)-5-methyl-oxazol-4-ylmethyl]-1H-indol-5-yl}-propionic acid as colorless solid.

MS: (M–H)⁻ 447.3.

Example 55
Rac-3-{1-[2-(2-Chloro-phenyl)-5-methyl-oxazol-4-ylmethyl]-1H-indol-5-yl}-2-isopropoxy-propionic Acid In analogy to the procedure described in example 44, rac-3-(1H-indol-5-yl)-2-isopropoxy-propionic acid methyl ester (preparation 8) was reacted with 4-chloromethyl-2-(2-chloro-phenyl)-5-methyl-oxazole to give rac-3-{1-[2-(2-chloro-phenyl)-5-methyl-oxazol-4-ylmethyl]-H-indol-5-yl}-2-isopropoxy-propionic acid as light brown solid.

MS: (M–H)⁻ 451.2.

Example 56
Rac-2-Isopropoxy-3-{1-[5-methyl-2-(4-trifluoromethyl-phenyl)-oxazol-4-ylmethyl]-1H-indol-5-yl}-propionic Acid In analogy to the procedure described in example 44, rac-3-(1H-indol-5-yl)-2-isopropoxy-propionic acid methyl ester (preparation 8) was reacted with 4-chloromethyl-5-methyl-2-(4-trifluoromethyl-phenyl)-oxazole to give rac-2-isopropoxy-3-{1-[5-methyl-2-(4-trifluoromethyl-phenyl)-oxazol-4-ylmethyl]-1H-indol-5-yl}-propionic acid as colorless solid.

MS: (M–H)⁻ 485.4.

Example 57
Rac-2-But-3-enyloxy-3-[1-(5-methyl-2-o-tolyl-oxazol-4-ylmethyl)-1H-indol-5-yl]-propionic Acid In analogy to the procedure described in example 44, rac-2-but-3-enyloxy-3-(1H-indol-5-yl)-propionic acid methyl ester (preparation 9) was reacted with 4-chloromethyl-5-methyl-2-o-tolyl-oxazole to give rac-2-but-3-enyloxy-3-[1-(5-methyl-2-o-tolyl-oxazol-4-ylmethyl)-1H-indol-5-yl]-propionic acid as light brown solid.

MS: (M–H)⁻ 443.3.

Example 58
Rac-2-But-3-enyloxy-3-{1-[2-(2-methoxy-phenyl)-5-methyl-oxazol-4-ylmethyl]-1H-indol-5-yl}-propionic Acid In analogy to the procedure described in example 44, rac-2-but-3-enyloxy-3-(1H-indol-5-yl)-propionic acid methyl ester (preparation 9) was reacted with 4-chloromethyl-2-(2-methoxy-phenyl)-5-methyl-oxazole to give rac-2-but-3-enyloxy-3-{1-[2-(2-methoxy-phenyl)-5-methyl-oxazol-4-ylmethyl]-1H-indol-5-yl}-propionic acid as light brown oil.

MS: (M–H)⁻ 459.3.

Example 59
Rac-2-But-3-enyloxy-3-{1-[2-(2-chloro-phenyl)-5-methyl-oxazol-4-ylmethyl]-1H-indol-5-yl}-propionic Acid In analogy to the procedure described in example 44, rac-2-but-3-enyloxy-3-(1H-indol-5-yl)-propionic acid methyl ester (preparation 9) was reacted with 4-chloromethyl-2-(2-chloro-phenyl)-5-methyl-oxazole to give rac-2-but-3-enyloxy-3-{1-[2-(2-chloro-phenyl)-5-methyl-oxazol-4-ylmethyl]-1H-indol-5-yl}-propionic acid as light yellow solid.

MS: (M–H)⁻ 463.2.

Example 60
Rac-2-But-3-enyloxy-3-{1-[5-methyl-2-(4-trifluoromethyl-phenyl)-oxazol-4-ylmethyl]-1H-indol-5-yl}-propionic Acid In analogy to the procedure described in example 44, rac-2-but-3-enyloxy-3-(1H-indol-5-yl)-propionic acid methyl ester (preparation 9) was reacted with 4-chloromethyl-5-methyl-2-(4-trifluoromethyl-phenyl)-oxazole to give rac-2-but-3-enyloxy-3-{1-[5-methyl-2-(4-trifluoromethyl-phenyl)-oxazol-4-ylmethyl]-1H-indol-5-yl}-propionic acid as light yellow solid.
MS: (M–H)⁻ 497.3.

Example 61
Rac-2-Ethoxy-3-{2-methyl-1-[2-(5-methyl-2-phenyl-oxazol-4-{1)-ethyl]-1H-indol-5-yl}-propionic Acid In analogy to the procedure described in example 44, rac-2-ethoxy-3-(2-methyl-1H-indol-5-yl)-propionic acid ethyl ester (preparation 5) was reacted with methanesulfonic acid 2-(5-methyl-2-phenyl-oxazol-4-yl)-ethyl ester to give rac-2-ethoxy-3-{2-methyl-1-[2-(5-methyl-2-phenyl-oxazol-4-yl)-ethyl]-1H-indol-5-yl}-propionic acid as light yellow viscous oil.
MS: (M+H)⁺ 433.3.

Example 62
Rac-2-Ethoxy-3-{2-methyl-1-[3-(5-methyl-2-phenyl-oxazol-4-yl)-propyl]-1H-indol-5-yl}-propionic Acid In analogy to the procedure described in example 44, rac-2-ethoxy-3-(2-methyl-1H-indol-5-yl)-propionic acid ethyl ester (preparation 5) was reacted with methanesulfonic acid 3-(5-methyl-2-phenyl-oxazol-4-yl)-propyl ester to give rac-2-ethoxy-3-{2-methyl-1-[3-(5-methyl-2-phenyl-oxazol-4-yl)-propyl]-1H-indol-5-yl}-propionic acid as orange viscous oil.
MS: (M–H)⁻ 445.3.

Example 63
Rac-2-Ethoxy-3-{4-methyl-1-[5-methyl-2-(4-trifluoromethyl-phenyl)-oxazol-4-ylmethyl]-1H-indol-5-yl}-propionic Acid In analogy to the procedure described in example 44, rac-2-ethoxy-3-(4-methyl-1H-indol-5-yl)-propionic acid ethyl ester [preparation 10h)] was reacted with 4-chloromethyl-5-methyl-2-(4-trifluoromethyl-phenyl)-oxazole to give rac-2-ethoxy-3-{4-methyl-1-[5-methyl-2-(4-trifluoromethyl-phenyl)-oxazol-4-ylmethyl]-1H-indol-5-yl}-propionic acid as yellow solid.
MS: (M–H)⁻ 485.3.

Example 64
Rac-2-Ethoxy-3-{1-[2-(4-isopropyl-phenyl)-5-methyl-oxazol-4-ylmethyl]-4-methyl-1H-indol-5-yl}-propionic Acid In analogy to the procedure described in example 44, rac-2-ethoxy-3-(4-methyl-1H-indol-5-yl)-propionic acid ethyl ester [preparation 10h)] was reacted with 4-chloromethyl-2-(4-isopropyl-phenyl)-5-methyl-oxazole to give rac-2-ethoxy-3-{1-[2-(4-isopropyl-phenyl)-5-methyl-oxazol-4-ylmethyl]-4-methyl-1H-indol-5-yl}-propionic acid as light yellow solid.
MS: (M–H)⁻ 459.3.

Example 65
Rac-2-Ethoxy-3-{1-[2-(4-fluoro-3-methyl-phenyl)-5-methyl-oxazol-4-ylmethyl]-4-methyl-1H-indol-5-yl}-propionic Acid In analogy to the procedure described in example 44, rac-2-ethoxy-3-(4-methyl-1H-indol-5-yl)-propionic acid ethyl ester [preparation 10h)] was reacted with 4-chloromethyl-2-(4-fluoro-3-methyl-phenyl)-5-methyl-oxazole to give rac-2-ethoxy-3-{-[2-(4-fluoro-3-methyl-phenyl)-5-methyl-oxazol-4-ylmethyl]-4-methyl-1H-indol-5-yl}-propionic acid as yellow solid.
MS: (M–H)⁻ 449.3.

Example 66
Rac-3-{1-[2-(2-Chloro-phenyl)-5-methyl-oxazol-4-ylmethyl]-4-methyl-1H-indol-5-yl}-2-ethoxy-propionic Acid In analogy to the procedure described in example 44, rac-2-ethoxy-3-(4-methyl-1H-indol-5-yl)-propionic acid ethyl ester [preparation 10h)] was reacted with 4-chloromethyl-2-(2-chloro-phenyl)-5-methyl-oxazole to give rac-3-{1-[2-(2-chloro-phenyl)-5-methyl-oxazol-4-ylmethyl]-4-methyl-1H-indol-5-yl}-2-ethoxy-propionic acid as yellow solid.
MS: (M–H) 451.2.

Example 67
Rac-3-{1-[2-(3,5-Dimethoxy-phenyl)-5-methyl-oxazol-4-ylmethyl]-4-methyl-1H-indol-5-yl}-2-ethoxy-propionic Acid In analogy to the procedure described in example 44, rac-2-ethoxy-3-(4-methyl-1H-indol-5-yl)-propionic acid ethyl ester [preparation 10h)] was reacted with 4-chloromethyl-2-(3,5-dimethoxy-phenyl)-5-methyl-oxazole to give rac-3-{1-[2-(3,5-dimethoxy-phenyl)-5-methyl-oxazol-4-ylmethyl]-4-methyl-1H-indol-5-yl}-2-ethoxy-propionic acid as yellow solid.
MS: (M–H)⁻ 477.2.

Example 68
Rac-2-Ethoxy-3-{1-[4-methyl-2-(4-trifluoromethyl-phenyl)-thiazol-5-ylmethyl]-1H-indol-5-yl}-propionic Acid In analogy to the procedures described in examples 36a) and 36b), rac-2-ethoxy-3-(1H-indol-5-yl)-propionic acid ethyl ester [preparation 1] was reacted with 5-chloromethyl-4-methyl-2-(4-trifluoromethyl-phenyl)-thiazole [PCT Int. Appl. (2001), WO 01/00603 A1] to give rac-2-ethoxy-3-{1-[4-methyl-2-(4-trifluoromethyl-phenyl)-thiazol-5-ylmethyl]-1H-indol-5-yl}-propionic acid ethyl ester, which was subsequently saponified to yield the title compound as yellow solid.
MS: (M–H)⁻ 487.3.

Example 69
(Z)-3-{1-[2-(2-Chloro-phenyl)-5-methyl-oxazol-4-ylmethyl]-1H-indol-5-yl}-2-ethoxy acrylic Acid In analogy to the procedures described in examples 36a) and 36b), (Z)-2-ethoxy-3-(1H-indol-5-yl)-acrylic acid ethyl ester [preparation 1a)] was reacted with 4-chloromethyl-2-(2-chloro-phenyl)-5-methyl-oxazole to give (Z)-3-{1-[2-(2-chloro-phenyl)-5-methyl-oxazol-4-ylmethyl]-1H-indol-5-yl}-2-ethoxy-acrylic acid ethyl ester, which was subsequently saponified to yield the title compound as colorless solid.
MS: (M+H)⁺ 437.2; (M+Na)⁺ 459.2

Example 70
Rac-2-Ethoxy-3-{1-[2-(4-isopropyl-phenyl)-5-methyl-oxazol-4-ylmethyl]-1H-indol-6-yl}-propionic Acid In analogy to the procedure described in example 44, rac-2-ethoxy-3-(1H-indol-6-yl)-propionic acid ethyl ester (preparation 11) was reacted with 4-chloromethyl-2-(4- isopropyl-phenyl)-5-methyl-oxazole to give rac-2-ethoxy-3-{1-[2-(4-isopropyl-phenyl)-5-methyl-oxazol-4-ylmethyl]-1H-indol-6-yl}-propionic acid as light yellow viscous oil.

MS: (M–H)⁻ 445.4.

Example 71
Rac-3-{1-[2-(3,5-Dimethoxy-phenyl)-5-methyl-oxazol-4-ylmethyl]-1H-indol-6-yl}-2-ethoxy-propionic Acid In analogy to the procedure described in example 44, rac-2-ethoxy-3-(1H-indol-6-yl)-propionic acid ethyl ester (preparation 11) was reacted with 4-chloromethyl-2-(3,5-dimethoxy-phenyl)-5-methyl-oxazole to give rac-3-{1-[2-(3,5-dimethoxy-phenyl)-5-methyl-oxazol-4-ylmethyl]-1H-indol-6-yl}-2-ethoxy-propionic acid as yellow solid.

MS: (M–H)⁻ 463.3.

Example 72
Rac-2-Ethoxy-3-{1-[2-(4-isopropyl-phenyl)-thiazol-4-ylmethyl]-1H-indol-6-yl}-propionic Acid In analogy to the procedure described in example 44, rac-2-ethoxy-3-(1H-indol-6-yl)-propionic acid ethyl ester (preparation 11) was reacted with 4-chloromethyl-2-(4-isopropyl-phenyl)-thiazole to give rac-2-ethoxy-3-{1-[2-(4-isopropyl-phenyl)-thiazol-4-ylmethyl]-1H-indol-6-yl}-propionic acid as yellow viscous oil.

MS: (M–H)⁻ 447.2.

Example A

Tablets comprising the following ingredients can be manufactured in a conventional manner:

| Ingredients | Per tablet |
|---|---|
| Compound of -formula I | 10.0–100.0 mg |
| Lactose | 125.0 mg |
| Maize starch | 75.0 mg |
| Talc | 4.0 mg |
| Magnesium stearate | 1.0 mg |

Example B

Capsules comprising the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example C

Injection solutions comprising the following ingredients can be manufactured in a conventional manner:

| | |
|---|---|
| Compound of formula I | 3.0 mg |
| Gelatine | 150.0 mg |
| Sodium carbonate | to obtain a final pH of 7 |
| Phenol | 4.7 mg |
| Water for injection solutions | ad 1.0 ml |

What is claimed is:

1. A compound of formula

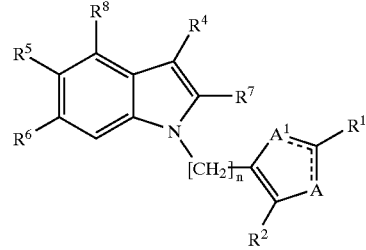

(I)

wherein $R^1$ is aryl or heteroaryl;

$R^2$ is hydrogen, alkyl or cycloalkyl;

$R^3$ is aryloxy, alkenyloxy, alkoxy or alkoxy substituted with one to three halogen atoms;

$R^4$ is hydrogen, alkyl or cycloalkyl;

wherein any one of $R^5$ and $R^6$ is

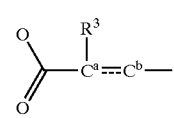

and the other is hydrogen, alkyl or cycloalkyl and, wherein the bond between the carbon atoms $C^a$ and $C^b$ is a carbon carbon single or double bond;

$R^7$ is hydrogen, alkyl or cycloalkyl;

$R^8$ is hydrogen, alkyl or cycloalkyl;

wherein any one of A and $A^1$ is nitrogen and the other is oxygen or sulfur;

n is 1, 2 or 3;

or a pharmaceutically acceptable salt or ester thereof.

2. The compound according to claim 1, wherein $R^3$ is alkoxy or alkoxy substituted with one to three halogen atoms;

$R^5$ is

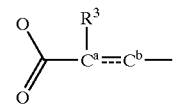

wherein the bond between the carbon atoms $C^a$ and $C^b$ is a carbon carbon single or double bond;

$R^6$ is hydrogen;

$R^7$ is hydrogen;

$R^8$ is hydrogen;

A is oxygen or sulfur; and $A^1$ is nitrogen;

or a pharmaceutically acceptable salt or ester thereof.

3. The compound according to claim 1, wherein $R^1$ is thiophenyl or phenyl, each of which is optionally substituted with one to three substituents independently selected from halogen, alkoxy, alkyl and alkyl substituted with one to three halogen atoms.

4. The compound according to claim 3, wherein $R^1$ is thiophenyl, phenyl or phenyl substituted with one to three substituents independently selected from fluoro, chloro, methoxy, ethoxy, propyloxy, isopropyloxy, methyl, ethyl, propyl, isopropyl, tert.-butyl, and trifluoromethyl.

5. The compound according to claim 1, wherein $R^2$ is hydrogen, methyl or ethyl.

6. The compound according to claim 5, wherein $R^2$ is methyl.

7. The compound according to claim 1, wherein $R^3$ is methoxy, ethoxy, propyloxy, isopropyloxy, phenoxy or butenyloxy.

8. The compound according to claim 7, wherein $R^3$ is methoxy or ethoxy.

9. The compound according to claim 1, wherein $R^4$ is hydrogen.

10. The compound according to claim 1, wherein $R^4$ is methyl.

11. The compound according to claim 1, wherein the bond between the carbon atoms $C^a$ and $C^b$ is a carbon carbon single bond.

12. The compound according to claim 1, wherein $R^6$ is hydrogen.

13. The compound according to claim 1, wherein $R^7$ is hydrogen.

14. The compound according to claim 1, wherein $R^7$ is methyl.

15. The compound according to claim 1, wherein $R^8$ is hydrogen.

16. The compound according to claim 1, wherein $R^8$ is methyl.

17. The compound according to claim 1, wherein A is oxygen or sulfur and $A^1$ is nitrogen.

18. The compound according to claim 17, wherein A is oxygen.

19. The compound according to claim 1, wherein n is 1.

20. The compound according to claim 1 which is
(S)-3-{1-[2-(2-Chloro-phenyl)-5-methyl-oxazol-4-ylmethyl]-1H-indol-5-yl}-2-ethoxy-propionic acid.

21. The compound according to claim 1 which is
(S)-2-Ethoxy-3-{1-[2-(2-methoxy-phenyl)-5-methyl-oxazol-4-ylmethyl]-1H-indol-5-yl}-propionic acid.

22. The compound according to claim 1 which is
(S)-2-Ethoxy-3-{1-[5-methyl-2-(4-trifluoromethyl-phenyl)-oxazol-4-ylmethyl]-1H-indol-5-yl}-propionic acid.

23. The compound according to claim 1 which is
(S)-3-{1-[2-(3,5-Dimethoxy-phenyl)-5-methyl-oxazol-4-ylmethyl]-1H-indol-5-yl}-2-ethoxy-propionic acid.

24. The compound according to claim 1 which is
(S)-2-Ethoxy-3-{1-[2-(4-fluoro-3-methyl-phenyl)-5-methyl-oxazol-4-ylmethyl]-1H-indol-5-yl}-propionic acid.

25. The compound according to claim 1 which is
rac-2-Ethoxy-3-{3-methyl-1-[5-methyl-2-(4-trifluoromethyl-phenyl)-oxazol-4-ylmethyl]-1H-indol-5-yl}-propionic acid.

26. The compound according to claim 1 which is
rac-3-{1-[2-(2-Chloro-phenyl)-5-methyl-oxazol-4-ylmethyl]-3-methyl-1H-indol-5-yl}-2-ethoxy-propionic acid.

27. The compound according to claim 1 which is
rac-2-Ethoxy-3-{1-[2-(4-fluoro-3-methyl-phenyl)-5-methyl-oxazol-4-ylmethyl]-3-methyl-1H-indol-5-yl}-propionic acid.

28. The compound according to claim 1 which is
rac-3-{1-[5-Methyl-2-(4-trifluoromethyl-phenyl)-oxazol-4-ylmethyl]-1H-indol-5-yl}-2-propoxy-propionic acid.

29. The compound according to claim 1 which is
rac-2-Isopropoxy-3-{1-[5-methyl-2-(4-trifluoromethyl-phenyl)-oxazol-4-ylmethyl]-1H-indol-5-yl}-propionic acid.

30. The compound according to claim 1 which is
rac-2-But-3-enyloxy-3-{1-[5-methyl-2-(4-trifluoromethyl-phenyl)-oxazol-4-ylmethyl]-1H-indol-5-yl}-propionic acid.

31. The compound according to claim 1 which is
rac-2-Ethoxy-3-{1-[2-(4-isopropyl-phenyl)-5-methyl-oxazol-4-ylmethyl]-4-methyl-1H-indol-5-yl}-propionic acid.

32. The compound according to claim 1 selected from the group consisting of:
rac-2-Ethoxy-3-[1-(5-methyl-2-phenyl-oxazol-4-ylmethyl)-1H-indol-5-yl]-propionic acid;
(S)-2-Ethoxy-3-[1-(5-methyl-2-phenyl-oxazol-4-ylmethyl)-1H-indol-5-yl]-propionic acid;
rac-2-Ethoxy-3-{1-[2-(2-fluro-phenyl)-5-methyl-oxazol-4-ylmethyl]-1H-indol-5-yl}-propionic acid;
rac-3-{1-[2-(2-Chloro-phenyl)-5-methyl-oxazol-4-ylmethyl]-1H-indol-5-yl}-2-ethoxy-propionic acid;
rac-2-Ethoxy-3-[1-(5-methyl-2-o-tolyl-oxazol-4-ylmethyl)-1H-indol-5-yl]-propionic acid;
rac-2-Ethoxy-3-{1-[2-(2-methoxy-phenyl)-5-methyl-oxazol-4-ylmethyl]-1H-indol-5-yl}-propionic acid;
rac-2-Ethoxy-3-{1-[2-(2-isopropoxy-phenyl)-5-methyl-oxazol-4-ylmethyl]-1H-indol-5-yl}-propionic acid;
rac-3-{1-[2-(3-Chloro-phenyl)-5-methyl-oxazol-4-ylmethyl]-1H-indol-5-yl}-2-ethoxy-propionic acid;
rac-2-Ethoxy-3-{1-[2-(4-ethyl-phenyl)-5-methyl-oxazol-4-ylmethyl]-1H-indol-5-yl}-propionic acid; and
(S)-2-Ethoxy-3-{1-[2-(4-ethyl-phenyl)-5-methyl-oxazol-4-ylmethyl]-1H-indol-5-yl}-propionic acid.

33. The compound according to claim 1 selected from the group consisting of:
(R)-2-Ethoxy-3-{1-[2-(4-ethyl-phenyl)-5-methyl-oxazol-4-ylmethyl]-1H-indol-5-yl}-propionic acid;
rac-2-Ethoxy-3-{1-[2-(4-isopropyl-phenyl)-5-methyl-oxazol-4-ylmethyl]-1H-indol-5-yl}-propionic acid;
rac-3-{1-[2-(4-tert-Butyl-phenyl)-5-methyl-oxazol-4-ylmethyl]-1H-indol-5-yl}-2-ethoxy-propionic acid;
rac-2-Ethoxy-3-{1-[2-(4-fluoro-phenyl)-5-methyl-oxazol-4-ylmethyl]-1H-indol-5-yl}-propionic acid;
rac-2-Ethoxy-3-{1-[5-methyl-2-(4-trifluoromethyl-phenyl)-oxazol-4-ylmethyl]-1H-indol-5-yl}-propionic acid;
rac-3-{1-[2-(3,5-Dimethyl-phenyl)-5-methyl-oxazol-4-ylmethyl]-1H-indol-5-yl}-2-ethoxy-propionic acid;
rac-3-{1-[2-(3,5-Dimethoxy-phenyl)-5-methyl-oxazol-4-ylmethyl]-1H-indol-5-yl}-2-ethoxy-propionic acid;
rac-3-{1-[2-(3,5-Difluoro-phenyl)-5-methyl-oxazol-4-ylmethyl]-1H-indol-5-yl}-2-ethoxy-propionic acid;
rac-3-{1-[2-(3,5-Dichloro-phenyl)-5-methyl-oxazol-4-ylmethyl]-1H-indol-5-yl}-2-ethoxy-propionic acid; and
rac-2-Ethoxy-3-{1-[2-(4-fluoro-3-methyl-phenyl)-5-methyl-oxazol-4-ylmethyl]-1H-indol-5-yl}-propionic acid.

34. The compound according to claim 1 selected from the group consisting of:
rac-2-Ethoxy-3-[1-(5-methyl-2-thiophen-2-yl-oxazol-4-ylmethyl)-1H-indol-5-yl]-propionic acid;
rac-2-Ethoxy-3-{1-[2-(3,4,5-trimethoxy-phenyl)-5-methyl-oxazol-4-ylmethyl]-1H-indol-5-yl}-propionic acid;

rac-2-Ethoxy-3-[1-(2-phenyl-oxazol-4-ylmethyl)-1H-indol-5-yl]-propionic acid;

rac-2-Ethoxy-3-[1-(2-phenyl-thiazol-4-ylmethyl)-1H-indol-5-yl]-propionic acid;

rac-2-Ethoxy-3-[1-(5-methyl-2-phenyl-thiazol-4-ylmethyl)-1H-indol-5-yl]-propionic acid;

rac-3-{1-[2-(4-Chloro-phenyl)-thiazol-4-ylmethyl]-1H-indol-5-yl}-2-ethoxy-propionic acid;

(Z)-2-Methoxy-3-[1-(5-methyl-2-phenyl-oxazol-4-ylmethyl)-1H-indol-5-yl]-acrylic acid;

rac-2-Methoxy-3-[1-(5-methyl-2-phenyl-oxazol-4-ylmethyl)-1H-indol-5-yl]-propionic acid;

(Z)-2-Methoxy-3-{1-[2-(5-methyl-2-phenyl-oxazol-4-yl)-ethyl]-1H-indol-5-yl}-acrylic acid; and rac-2-Methoxy-3-{1-[2-(5-methyl-2-phenyl-oxazol-4-yl)-ethyl]-1H-indol-5-yl}-propionic acid.

35. The compound according to claim 1 selected from the group consisting of:

rac-2-Ethoxy-3-{1-[2-(4-isopropyl-phenyl)-5-methyl-oxazol-4-ylmethyl]-3-methyl-1H-indol-5-yl}-propionic acid;

rac-2-Ethoxy-3-{2-methyl-1-[5-methyl-2-(4-trifluoromethyl-phenyl)-oxazol-4-ylmethyl]-1H-indol-5-yl}-propionic acid;

rac-2-Ethoxy-3-{1-[2-(4-isopropyl-phenyl)-5-methyl-oxazol-4-ylmethyl]-2-methyl-1H-indol-5-yl}-propionic acid;

rac-2-Ethoxy-3-{1-[2-(4-fluoro-3-methyl-phenyl)-5-methyl-oxazol-4-ylmethyl]-2-methyl-1H-indol-5-yl}-propionic acid;

rac-3-{1-[2-(2-Chloro-phenyl)-5-methyl-oxazol-4-ylmethyl]-2-methyl-1H-indol-5-yl}-2-ethoxy-propionic acid;

rac-2-Ethoxy-3-[2-methyl-1-(2-phenyl-thiazol-4-ylmethyl)-1H-indol-5-yl]-propionic acid;

rac-3-{1-[2-(4-tert-Butyl-phenyl)-oxazol-4-ylmethyl]-2-methyl-1H-indol-5-yl}-2-ethoxy-propionic acid;

rac-3-[1-(5-Methyl-2-o-tolyl-oxazol-4-yl methyl)-1H-indol-5-yl]-2-propoxy-propionic acid;

rac-3-{1-[2-(2-Methoxy-phenyl)-5-methyl-oxazol-4-ylmethyl]-1H-indol-5-yl}-2-propoxy-propionic acid; and rac-3-{1-[5-Methyl-2-(4-trifluoromethyl-phenyl)-oxazol-4-ylmethyl]-1H-indol-5-yl}-2-phenoxy-propionic acid.

36. The compound according to claim 1 selected from the group consisting of:

rac-3-{1-[2-(4-Isopropyl-phenyl)-5-methyl-oxazol-4-ylmethyl]-1H-indol-5-yl}-2-phenoxy-propionic acid;

rac-3-{1-[2-(2-Chloro-phenyl)-5-methyl-oxazol-4-ylmethyl]-1H-indol-5-yl}-2-phenoxy-propionic acid;

rac-3-{1-[2-(4-Fluoro-3-methyl-phenyl)-5-methyl-oxazol-4-ylmethyl]-1H-indol-5-yl}-2-phenoxy-propionic acid;

rac-2-Isopropoxy-3-[1-(5-methyl-2-o-tolyl-oxazol-4-ylmethyl)-1H-indol-5-yl]-propionic acid;

rac-2-Isopropoxy-3-{1-[2-(2-methoxy-phenyl)-5-methyl-oxazol-4-ylmethyl]-1H-indol-5-yl}-propionic acid;

rac-3-{1-[2-(2-Chloro-phenyl)-5-methyl-oxazol-4-ylmethyl]-1H-indol-5-yl}-2-isopropoxy-propionic acid;

rac-2-But-3-enyloxy-3-[1-(5-methyl-2-o-tolyl-oxazol-4-ylmethyl)-1H-indol-5-yl]-propionic acid;

rac-2-But-3-enyloxy-3-{1-[2-(2-methoxy-phenyl)-5-methyl-oxazol-4-ylmethyl]-1H-indol-5-yl}-propionic acid;

rac-2-But-3-enyloxy-3-{1-[2-(2-chloro-phenyl)-5-methyl-oxazol-4-ylmethyl]-1H-indol-5-yl}-propionic acid; and rac-2-Ethoxy-3-{2-methyl-1-[2-(5-methyl-2-phenyl-oxazol-4-yl)-ethyl]-1H-indol-5-yl}-propionic acid.

37. The compound according to claim 1 selected from the group consisting of:

rac-2-Ethoxy-3-{2-methyl-1-[3-(5-methyl-2-phenyl-oxazol-4-yl)-propyl]-1H-indol-5-yl}-propionic acid;

rac-2-Ethoxy-3-{4-methyl-1-[5-methyl-2-(4-trifluoromethyl-phenyl)-oxazol-4-ylmethyl]-1H-indol-5-yl}-propionic acid;

rac-2-Ethoxy-3-{1-[2-(4-fluoro-3-methyl-phenyl)-5-methyl-oxazol-4-ylmethyl]-4-methyl-1H-indol-5-yl}-propionic acid;

rac-3-{1-[2-(2-Chloro-phenyl)-5-methyl-oxazol-4-ylmethyl]-4-methyl-1H-indol-5-yl}-2-ethoxy-propionic acid;

rac-3-{1-[2-(3,5-Dimethoxy-phenyl)-5-methyl-oxazol-4-ylmethyl]-4-methyl-1H-indol-5-yl}-2-ethoxy-propionic acid;

rac-2-Ethoxy-3-{1-[4-methyl-2-(4-trifluoromethyl-phenyl)-thiazol-5-ylmethyl]-1H-indol-5-yl}-propionic acid;

(Z)-3-{1-[2-(2-Chloro-phenyl)-5-methyl-oxazol-4-ylmethyl]-1H-indol-5-yl}-2-ethoxy-acrylic acid;

rac-2-Ethoxy-3-{1-[2-(4-isopropyl-phenyl)-5-methyl-oxazol-4-ylmethyl]-1H-indol-6-yl}-propionic acid;

rac-3-{1-[2-(3,5-Dimethoxy-phenyl)-5-methyl-oxazol-4-ylmethyl]-1H-indol-6-yl}-2-ethoxy-propionic acid; and rac-2-Ethoxy-3-{1-[2-(4-isopropyl-phenyl)-thiazol-4-ylmethyl]-1H-indol-6-yl}-propionic acid.

38. A pharmaceutical composition comprising a compound in accordance with claim 1 or a pharmaceutically acceptable salt thereof, and a therapeutically inert carrier.

39. The pharmaceutical composition of claim 38 further comprising a therapeutically effective amount of orlistat.

40. A method for the treatment of non-insulin dependent diabetes mellitus in a patient in need of treatment, comprising administering to said patient from about 0.1 mg to about 1000 mg per day of a compound according to claim 1 or a pharmaceutically acceptable salt thereof.

41. The method according to claim 40, wherein said compound or salt thereof is administered in an amount of from about 1 mg to about 100 mg per day.

42. The method according to claim 40, further comprising administering to said patient from 60 mg to 720 mg orlistat per day.

* * * * *